United States Patent
Khanna et al.

(10) Patent No.: US 11,066,711 B2
(45) Date of Patent: Jul. 20, 2021

(54) **BIOMARKERS FOR PREDICTING *CLOSTRIDIUM DIFFICILE* INFECTION TREATMENT OUTCOME**

(71) Applicant: Mayo Foundation for Medical Education and Research, Rochester, MN (US)

(72) Inventors: Sahil Khanna, Rochester, MN (US); Purna C. Kashyap, Rochester, MN (US); Darrell S. Pardi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 51 days.

(21) Appl. No.: 16/060,152

(22) PCT Filed: Dec. 8, 2016

(86) PCT No.: PCT/US2016/065566
§ 371 (c)(1),
(2) Date: Jun. 7, 2018

(87) PCT Pub. No.: WO2017/100420
PCT Pub. Date: Jun. 15, 2017

(65) Prior Publication Data
US 2018/0363033 A1 Dec. 20, 2018

Related U.S. Application Data

(60) Provisional application No. 62/264,479, filed on Dec. 8, 2015.

(51) Int. Cl.
| | | |
|---|---|---|
| *C12Q 1/689* | (2018.01) |
| *G01N 33/569* | (2006.01) |
| *A61K 31/4164* | (2006.01) |
| *A61K 31/7048* | (2006.01) |
| *A61K 38/17* | (2006.01) |
| *A61K 35/74* | (2015.01) |

(52) U.S. Cl.
CPC .......... *C12Q 1/689* (2013.01); *A61K 31/4164* (2013.01); *A61K 31/7048* (2013.01); *A61K 35/74* (2013.01); *A61K 38/1774* (2013.01); *G01N 33/56911* (2013.01); *C12Q 2600/106* (2013.01); *C12Q 2600/118* (2013.01); *G01N 2333/33* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 8,906,668 B2* | 12/2014 | Henn | ..................... | A23L 33/127 |
| | | | | 435/252.4 |
| 9,028,841 B2* | 5/2015 | Henn | ..................... | A61K 9/4891 |
| | | | | 424/247.1 |
| 9,533,014 B2* | 1/2017 | Henn | ..................... | A23L 33/135 |
| 9,585,921 B2* | 3/2017 | McKenzie | ............. | A61K 35/74 |
| 9,802,988 B2* | 10/2017 | Donnenberg | .......... | C07K 14/33 |
| 10,300,043 B2* | 5/2019 | Kashyap | ................ | A61K 35/74 |
| 10,758,529 B2* | 9/2020 | Reddy | .................. | A61K 9/0053 |
| 2013/0064105 A1* | 3/2013 | Huang | ..................... | H04L 65/80 |
| | | | | 370/252 |
| 2013/0224155 A1 | 8/2013 | Kaplan et al. | | |
| 2014/0199281 A1 | 7/2014 | Henn et al. | | |
| 2014/0219966 A1 | 8/2014 | Boone et al. | | |
| 2015/0344940 A1 | 12/2015 | Savidge et al. | | |
| 2018/0100009 A1* | 4/2018 | Crowe | ............... | C07K 16/1282 |
| 2018/0353575 A1* | 12/2018 | Fischetti | .................. | A61P 1/00 |
| 2018/0363033 A1* | 12/2018 | Khanna | ............ | G01N 33/56911 |
| 2019/0216861 A1* | 7/2019 | Kashyap | ............... | A61K 35/741 |
| 2019/0298735 A1* | 10/2019 | Aronoff | ............. | A61K 31/5575 |
| 2019/0350987 A1* | 11/2019 | Goodman | ................ | C12R 1/01 |
| 2019/0350988 A1* | 11/2019 | Henn | ...................... | A23P 10/30 |
| 2019/0381113 A1* | 12/2019 | Pamer | ..................... | C12Q 1/26 |
| 2020/0368295 A1* | 11/2020 | Santiago | ............... | A61K 35/741 |

FOREIGN PATENT DOCUMENTS

| | | | | |
|---|---|---|---|---|
| WO | WO 2014/153194 | | 9/2014 | |
| WO | WO-2016156474 A1 * | 10/2016 | ......... | C07K 16/1282 |
| WO | WO-2017053544 A1 * | 3/2017 | ........... | A61K 35/741 |
| WO | WO-2017100420 A1 * | 6/2017 | ............. | A61K 35/74 |
| WO | WO-2019152667 A1 * | 8/2019 | ......... | C07K 16/2818 |
| WO | WO-2019157003 A1 * | 8/2019 | ............... | C12R 1/01 |

OTHER PUBLICATIONS

Cheng et al, Am. J. Transplant., 2019, 19:501-511, (Year: 2019).*
Dubberke et al. Clinical Infectious Diseases, Oct. 15, 2018, 67/8:1198-1204. published online: Mar. 29, 2018 (Year: 2018).*
Dutta et al, Clinical Gastroenterology and Hepatology, Sep. 2014, 12/9:1572-1576. (Year: 2014).*
Khanna et al, Clinical Infectious Diseases, May 15, 2013, 56/10:1401-1406. electronically published Feb. 13, 2013. (Year: 2013).*
Khanna et al, Mayo Clinic PRoc., Nov. 2012, 87/11:1106-1117 (Year: 2012).*
Khanna et al., Nat. Rev. Gastroenterol. Hepatol., Jun. 2012. 9:307-308. published online: May 15, 2012 (Year: 2012).*
Khanna et al, Microbiome, 2017, 5:55, 8 pages, published online: May 15, 2017 (Year: 2017).*

(Continued)

*Primary Examiner* — Nita M. Minnifield
(74) *Attorney, Agent, or Firm* — Fish & Richardson P.C.

(57) ABSTRACT

Provided herein are biomarkers that can be altered in the gut of a mammal having CDI. One or more biomarkers can be used to predict *Clostridium difficile* infection (CDI) treatment outcome (e.g., response to primary CDI treatment and/or risk of recurrence after primary CDI treatment) in a mammal (e.g., a human) having CDI. Methods for using one or more biomarkers can be used to predict response to primary CDI treatment in a mammal having CDI. Methods for using one or more biomarkers can be used to predict risk of recurrence in a mammal having CDI. Also provided are methods of treating CDI.

9 Claims, 17 Drawing Sheets

(56) References Cited

OTHER PUBLICATIONS

Laanani et al, Am J Gastroenterol, Apr. 2020;115:537-547. published online: Mar. 6, 2020 https://doi.org/10.14309/ajg.0000000000000574 (Year: 2020).*

Malinowski et al, CurrOpin Gastroenterol. Jan. 2017, 33/1:8-13 (Year: 2017).*

Saffouri et al, American Journal of Gastroenterology, Jun. 2014, 109:924-925 (Year: 2014).*

Spiceland et al, J Clin Gastroenterol Feb. 2018;52:151-154 (Year: 2018).*

Stalley et al, Gut Microbes, 2017, 8/3:276-288. published online: Mar. 10, 2017 (Year: 2017).*

Tariq et al, Clinical Infectious Diseases, Nov. 15, 2017;65(10):1745-7. published online: Jul. 18, 2017 (Year: 2017).*

Pardi et al, Abstracts of the Interscience Conference on Antimicrobial Agents and Chemotherapy. Sep. 5-9, 2014, vol. 54, p. B-1875a. Abstract only (Year: 2014).*

Khanna et al, American Journal of Gasteroenterology, Oct. 2013, vol. 108, Suppl. 1. pp. S508, Abstract# 1688. Abstract only (Year: 2013).*

Anderson, "A new method for non-parametric multivariate analysis of variance," Austral Ecology, Feb. 2001, 26(1):32-46.

Antharam et al., "Intestinal dysbiosis and depletion of butyrogenic bacteria in Clostridium difficile infection and nosocomial diarrhea," J. Clin. Microbiol., Jun. 2013, 51:2884-92.

Cao et al., "Association between Faecalibacterium prausnitzii reduction and inflammatory bowel disease: a meta-analysis and systematic review of the literature," Gastroenterol. Res. Pract., Mar. 2014, 2014:872725.

Caporaso et al., "QIIME allows analysis of high-throughput community sequencing data," Nat. Methods, May 2010, 7(5):335-6.

Chang et al., "Decreased Diversity of the Fecal Microbiome in Recurrent Clostridium difficile—Associated Diarrhea," J. Infect. Dis., Feb. 2008, 197(3):435-8.

Cohen et al., "Clinical practice guidelines for Clostridium difficile infection in adults: 2010 update by the society for healthcare epidemiology of America (SHEA) and the infectious diseases society of America (IDSA)," Infect. Control Hosp. Epidemiol., May 2010, 31(5):431-55.

Cohen et al., "Prevalence and characteristics of *Staphylococcus aureus* colonization among healthcare professionals in an urban teaching hospital," Infect. Control Hosp. Epidemiol, Jun. 2010, 31(6):431-55.

DeSantis et al., "Greengenes, a chimera-checked 16S rRNA gene database and workbench compatible with ARB," Appl. Environ. Microbiol., Jul. 2006, 72(7):5069-72.

Dethlefsen and Relman, "Incomplete recovery and individualized responses of the human distal gut microbiota to repeated antibiotic perturbation," Proc. Natl. Acad. Sci. USA., Mar. 2011, 108Suppl1:4554-61.

Eyre et al., "Predictors of first recurrence of Clostridium difficile infection: implications for initial management," Clin. Infect. Dis., Aug. 2012, 55Suppl2:577-87.

Ferreyra et al., "Gut microbiota-produced succinate promotes C. difficile infection after antibiotic treatment or motility disturbance," Cell Host. Microbe., Dec. 2014, 16(6):770-7.

Hamilton et al., "High-throughput DNA sequence analysis reveals stable engraftment of gut microbiota following transplantation of previously frozen fecal bacteria," Gut Microbes, Jan. 2013, 4(2):125-35.

Hu et al., "A prospective study of risk factors and historical trends in metronidazole failure for Clostridium difficile infection," Clin. Gastroenterol. Hepatol., Dec. 2008, 6(12):1354-60.

Hu et al., "Prospective derivation and validation of a clinical prediction rule for recurrent Clostridium difficile infection," Gastroenterology, Apr. 2009, 136(4):1206-14.

Johnson et al., "Vancomycin, metronidazole, or tolevamer for Clostridium difficile infection: results from two multinational, randomized, controlled trials," Clin. Infect. Dis., May 2014, 59(3):345-54.

Kelly et al., "Clostridium difficile—more difficult than ever," N. Engl. J. Med., Oct. 2008, 359(18):1932-40.

Kelly et al., "Update on fecal microbiota transplantation 2015: indications, methodologies, mechanisms, and outlook," Gastroenterology, Jul. 2015, 149(1):223-37.

Khanna et al., "Clostridium difficile infection: management strategies for a difficult disease," Therap. Adv. Gastroenterol, Mar. 2014, 7(2):72-86.

Khanna et al., "Gut microbiome predictors of treatment response and recurrence in primary Clostridium difficile infection," Aliment. Pharmacol. Ther., Oct. 2016; 44(7):715-727.

Khanna et al., "The epidemiology of community-acquired Clostridium difficile infection: a population-based study," Am. J. Gastroenterol, Jan. 2012, 107(1):89-95.

Khanna, "Gut Microbiota Changes as Predictors of Treatment Failure in Primary Clostridium difficile Infection," Poster, Presented at ACG 2015, Annual Scientific Meeting and Postgraduate Course, Oct. 16-21, 2015, Honolulu, HI.

Khoruts et al., "Changes in the composition of the human fecal microbiome after bacteriotherapy for recurrent Clostridium difficile-associated diarrhea," J. Clin. Gastroenterol, May 2010, 44(5):354-60.

Lawley et al., "Targeted restoration of the intestinal microbiota with a simple, defined bacteriotherapy resolves relapsing Clostridium difficile disease in mice," PLoS Pathog, Oct. 2012, 8(10):e1002995.

Leffler et al., "Clostridium difficile infection," N. Engl. J. Med., Apr. 2015, 372(16):1539-48.

Lessa et al., "Burden of Clostridium difficile infection in the United States," N. Engl. J. Med., Feb. 2015, 372(9):825-34.

Louie et al., "Fidaxomicin versus vancomycin for Clostridium difficile infection," N. Engl. J. Med., Feb. 2011, 364(5):422-31.

Lozupone et al., "UniFrac: an effective distance metric for microbial community comparison," ISME J., Feb. 2011, 5(2):169-72.

Magill et al., "Multistate point-prevalence survey of health care-associated infections," N. Engl. J. Med., Mar. 2014, 370(13):1198-208.

Manges et al., "Comparative metagenomic study of alterations to the intestinal microbiota and risk of nosocomial Clostridum difficile-associated disease," J. Infect Dis., Dec. 2010, 202(12):1877-84.

Nanwa et al., "The economic impact of Clostridium difficile infection: a systematic review," Am. J. Gastroenterol, Apr. 2015, 110(4):511-9.

PCT International Search Report in International Application No. PCT/US2016/065566 dated Apr. 17, 2017, 4 pages.

Pryde et al., "The microbiology of butyrate formation in the human colon," FEMS Microbiol. Lett., Dec. 2002, 217(2):133-9.

Rea et al., "Effect of broad-and narrow-spectrum antimicrobials on Clostridium difficile and microbial diversity in a model of the distal colon," Proc. Natl. Acad. Sci. USA.,Mar. 2011, 108Suppl1:4639-44.

Rios-Covian et al., "Enhanced butyrate formation by cross-feeding between Faecalibacterium prausnitzii and Bifidobacterium adolescentis," FEMS Microbiol. Lett., Nov. 2015, 362(21).

Seekatz and Young, "Clostridium difficile and the microbiota," J. Clin. Invest., Oct. 2014, 124(10):4182-9.

Segata et al., "Metagenomic biomarker discovery and explanation," Genome Biol., Jun. 2011, 12(6):R60.

Shankar et al., "Species and genus level resolution analysis of gut microbiota in Clostridium difficile patients following fecal microbiota transplantation," Microbiome, Dec. 2014, 2(1):13.

Shivashankar et al., "Clinical predictors of recurrent Clostridium difficile infection in out-patients," Aliment. Pharmacol. Ther., Sep. 2014, 40(5):518-22.

Sing et al., "ROCR: visualizing classifier performance in R," Bioinformatics, Oct. 2005, 21(20):3940-1.

Smoot et al., "Cytoscape 2.8: new features for data integration and network visualization," Bioinformatics, Feb. 2011, 27(3):431-2.

Surawicz et al., "Guidelines for diagnosis, treatment, and prevention of Clostridium difficile infections," Am. J. Gastroenterol, Apr. 2013, 108(4):478-98.

(56) References Cited

OTHER PUBLICATIONS

Weingarden et al., "Dynamic changes in short-and long-term bacterial composition following fecal microbiota transplantation for recurrent Clostridium difficile infection," Microbiome, Dec. 2015, 3(1):10.

Zar et al., "A comparison of vancomycin and metronidazole for the treatment of Clostridium difficile—associated diarrhea, stratified by disease severity," Clin. Infect Dis., Aug. 2007, 45(3):302-7.

* cited by examiner

BIOMARKERS FOR PREDICTING *CLOSTRIDIUM DIFFICILE* INFECTION TREATMENT OUTCOME

CROSS-REFERENCE TO RELATED APPLICATIONS

This application is a National Stage application under 35 U.S.C. § 371 of International Application No. PCT/US2016/065566, having an International Filing Date of Dec. 8, 2016, which claims the benefit of U.S. Patent Application Ser. No. 62/264,479, filed on Dec. 8, 2015. The disclosure of the prior application is considered part of (and is incorporated by reference in) the disclosure of this application.

TECHNICAL FIELD

This document relates to methods and materials for predicting *Clostridium difficile* infection (CDI) treatment outcome. For example, this document provides methods for using one or more biomarkers to predict a response to primary CDI treatment and/or to predict risk of recurrence after primary CDI treatment in a mammal (e.g., a human).

BACKGROUND

CDI is the most common hospital-acquired infection and a leading cause of diarrhea in the United States with an estimated 450,000 infections per year and over 29,000 deaths attributed to CDI (Kelly et al., 2008 *N Engl J Med* 359:1932-40; Magill et al., 2014 *N Engl J Med* 370:1198-208; and Lessa et al., 2015 *N Engl J Med* 372:825-34). Despite advancements in drug therapy and the emergence of standard treatment guidelines, CDI is associated with several adverse outcome including the development of severe-complicated CDI (up to 5%), treatment failure (up to 15%) and recurrent CDI (up to 60% or higher after 3 episodes) (Leffler et al., 2015 *N Engl J Med* 372:1539-48; Khanna et al., 2014 *Therap Adv Gastroenterol* 7:72-86). CDI also has a tremendous economic impact with attributable costs ranging from $8,911 to $30,049 for hospitalized patients with CDI (Nanwa et al., 2015 *Am J Gastroenterol* 110:511-9).

SUMMARY

There are several clinical models to predict the risk of recurrent CDI, although none are robust enough for routine clinical use and there are no models to predict treatment response after initial antibiotic therapy.

This document relates to biomarkers and methods for predicting CDI treatment outcome. There are no clinically used robust models to predict treatment failure or recurrent CDI after initial antibiotic treatment and as a result 5-35% patients have to undergo prolonged treatment trials prior to receiving effective treatment.

Provided herein are materials (e.g., biomarkers) and methods to predict CDI treatment outcome (e.g., response to primary CDI treatment and/or risk of recurrence after primary CDI treatment). As described herein, microbial communities in patients with CDI were characterized to identify biomarkers that can be used to predict a response to primary CDI treatment and/or to predict risk of recurrence after primary CDI treatment in a mammal (e.g., a human). Biomarkers potentially allow identification of subsets patients that may be primarily treated with more effective therapies such as fecal microbiota transplantation or defined microbial consortia instead of a prolonged therapeutic trial with antibiotics.

This document provides methods for predicting response to primary CDI treatment in a mammal having CDI. Primary CDI treatment can include, for example, administration of a pharmaceutical (e.g., metronidazole, vancomycin, fidaxomicin, and combinations thereof). In some cases, a method for predicting response to primary CDI treatment can include detecting a gut microbiota panel in a fecal sample obtained from the mammal and identifying the mammal as being likely to respond to a primary CDI treatment if two or more gut microbiota in the panel are increased relative to a control gut microbiota panel (e.g. gut microbiota from one or more mammals that do not have CDI). Detecting a gut microbiota can include, for example, isolation of DNA from the fecal sample, identification of operational taxonomic units, and/or 16s sequencing. A gut microbiota panel for can include, for example, *Ruminococcaceae*, *Rikenellaceae*, *Clostridiaceae*, *Bacteroides*, *Faecalibacterium* (e.g., *Faecalibacterium prausnitzii*), and *Rothia* (e.g., *Rothia mucilaginosa*).

In some cases, a method for predicting response to primary CDI can include detecting a clinical parameter panel for the mammal and identifying the mammal as being likely to have primary CDI treatment failure if one or more of the clinical parameters are detected. A clinical parameter panel can include, for example, severe CDI, prior antibiotic (e.g., a β-lactam antibiotic such as a cephalosporin) use, and hospital-acquired *C. difficile*.

In some cases, a method for predicting response to primary CDI treatment can include detecting a mode of *C. difficile* acquisition and identifying the mammal as being likely to respond to a primary CDI treatment if the mode of *C. difficile* acquisition is community acquired *C. difficile*.

This document provides methods for predicting risk of recurrence in a mammal having CDI. In some cases, a method for predicting risk of recurrence in a mammal having CDI can include detecting a gut microbiota panel in a fecal sample obtained from the mammal and identifying the mammal as being likely to have CDI recurrence if two or more gut microbiota in the panel are increased relative to a control gut microbiota panel (e.g., gut microbiota from one or more mammals that do not have CDI). Detecting a gut microbiota can include, for example, isolation of DNA from the fecal sample, identification of operational taxonomic units, and/or 16s sequencing. A gut microbiota panel can include, for example, *Veillonella*, *Enterobacteriaceae*, *Streptococcus*, *Parabacteroides*, and *Lachnospiraceae*.

This document provides methods of treating CDI in a mammal. Methods of treating CDI can include primary CDI treatment or advanced CDI treatment. Primary CDI treatment can include, for example, administration of a pharmaceutical (e.g., metronidazole, vancomycin, fidaxomicin, and combinations thereof). Advanced CDI treatment can include, for example, fecal transplantation, immunoglobulin therapy, defined microbial consortia, and combinations thereof.

In some cases, a method of treating CDI in a mammal can include detecting a gut microbiota panel in a fecal sample obtained from the mammal and administering a primary CDI treatment to the mammal if two or more gut microbiota in the panel are increased relative to a control gut microbiota panel (e.g., gut microbiota from one or more mammals that do not have CDI). Detecting a gut microbiota can include, for example, isolation of DNA from the fecal sample, identification of operational taxonomic units, and/or 16s sequencing. Primary CDI treatment can include, for example, administration of a pharmaceutical selected from the group consisting of metronidazole, vancomycin, fidaxomicin, and combinations thereof. A gut microbiota panel can include, for example, *Ruminococcaceae, Rikenellaceae, Clostridiaceae, Bacteroides, Faecalibacterium*, and *Rothia*.

In some cases, a method of treating CDI can include detecting a clinical parameter (e.g., a mode of *C. difficile* acquisition) for the mammal and administering a primary CDI treatment to the mammal if the mode of *C. difficile* acquisition is community acquired *C. difficile*.

In some cases a method for treating CDI in a mammal can include detecting a gut microbiota panel in a fecal sample obtained from the mammal and administering advanced CDI treatment to the mammal if two or more gut microbiota in the panel are increased relative to a control gut microbiota panel (e.g., gut microbiota from one or more mammals that do not have CDI). Detecting a gut microbiota can include, for example, isolation of DNA from the fecal sample, identification of operational taxonomic units, and/or 16s sequencing. A gut microbiota panel can include, for example, *Veillonella* (e.g., *Veillonella dispar* or *Veillonella parvula*), *Enterobacteriaceae* (e.g., *Enterobacteriaceae envinia*), *Streptococcus, Parabacteroides* (e.g., *Parabacteroides distasonis*), and *Lachnospiraceae*.

In some cases, a method of treating CDI in a mammal can include detecting a panel of clinical parameters for the mammal and administering advanced CDI treatment to the mammal if one or more of the clinical parameters are detected. A panel of clinical parameters can include, for example, severe CDI, prior antibiotic (e.g., a β-lactam antibiotic such as a cephalosporin) use, and hospital-acquired *C. difficile*.

Methods provided herein can also include identifying the mammal (e.g., a human) as having CDI.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
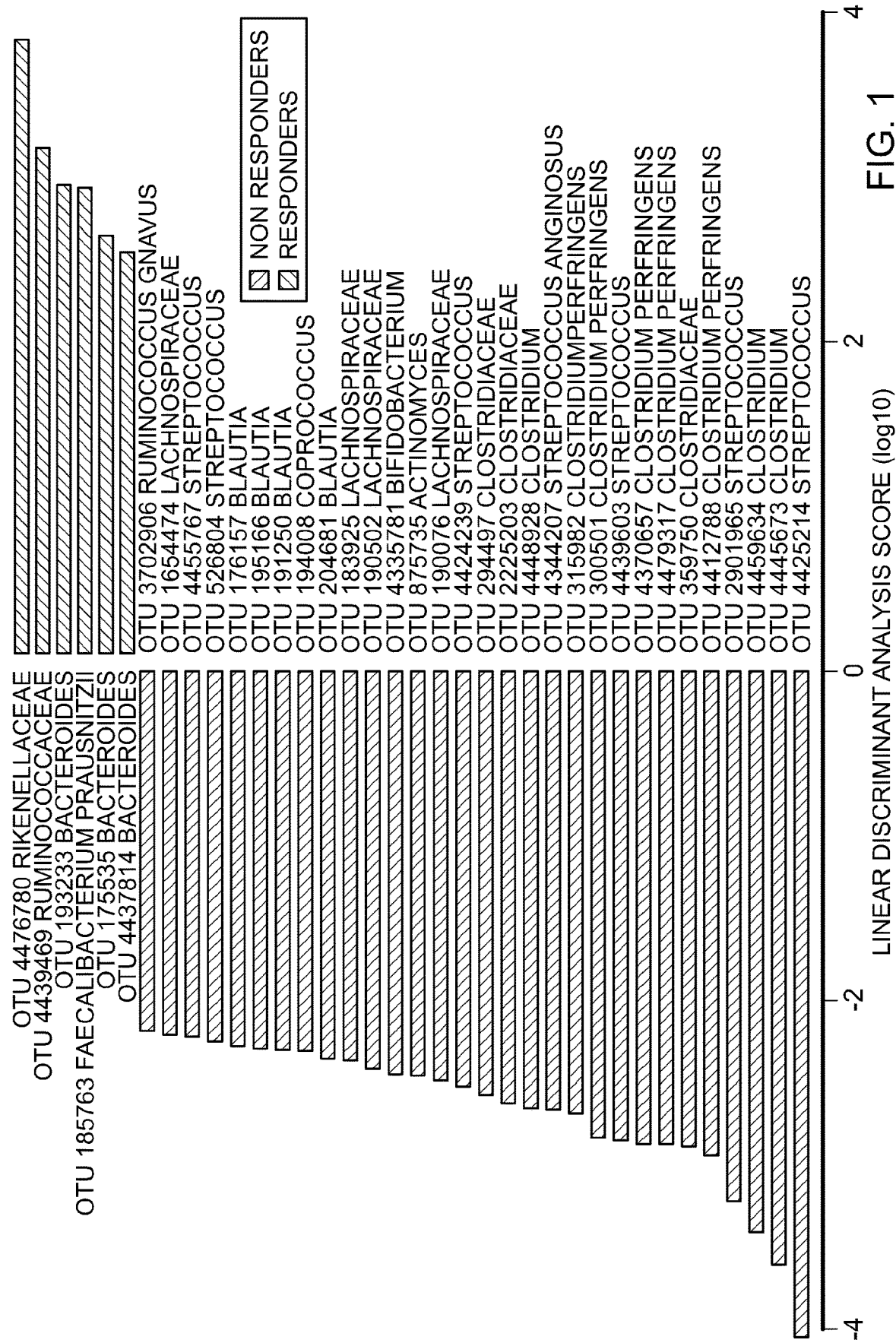
FIG. 1 shows a summary of the operational taxonomic units (OTUs) associated with response or non-response to treatment using Linear discriminant analysis Effect Size analysis. Representative bacteria with relative abundance of at least 1% with significant differences are represented.

This document provides methods and materials involved in predicting CDI treatment outcome (e.g., response to primary CDI treatment and/or risk of recurrence after primary CDI treatment) in a mammal (e.g., a human) having CDI. For example, this document provides one or more biomarkers that can be altered in the gut of a mammal having CDI. In some cases, this disclosure provides methods for using one or more biomarkers to predict response to primary CDI treatment in a mammal having CDI. In some cases, this disclosure provides methods to predict risk of recurrence in a mammal having CDI. In some cases, this disclosure provides methods of treating CDI.

Any type of mammal having CDI can be evaluated to predict CDI treatment outcome and/or treated as described herein. For example, humans and other primates such as monkeys having pancreatitis can be treated with one or more colipase inhibitors. In some cases, dogs, cats, horses, cows, pigs, sheep, rabbits, mice, and rats can be evaluated to predict CDI treatment outcome and/or treated as described herein.

Any appropriate method can be used to identify a mammal (e.g. a human) having CDI. For example, detection of bacterial polypeptides or toxins produced by *C. difficile* bacteria in a stool sample (e.g, by enzyme immunoassay, polymerase chain reaction, cell cytotoxicity assay, etc.) can be used to identify a human or other mammal as having CDI. In some cases, a CDI diagnosis may be confirmed using, for example, colon examinations and/or imaging tests.

Once identified as having CDI, a mammal can be evaluated to predict CDI treatment outcome (e.g., response to primary CDI treatment and/or risk of recurrence after primary CDI treatment). A mammal can be evaluated by, for example, detecting one or more biomarkers in a biological sample (e.g., a fecal sample) obtained from the mammal.

As used herein, a "biomarker" is a characteristic that can be objectively measured and evaluated as a predictor of treatment outcome (e.g., response to primary CDI treatment and/or risk of recurrence after primary CDI treatment). A biomarker that can be used to predict treatment outcome can include, for example, a bacterium (e.g., a gut bacterium), a clinical predictor (e.g., severity of CDI, prior antibiotic use, and/or mode of *C. difficile* acquisition), a microbiota functional repertoire (e.g., a polypeptide such as an enzyme) produced by a bacterium present in the gut, or combinations thereof. A biomarker panel can encompass any two or more (e.g., two, three, four, five, six, seven, eight, nine, ten, or more) of the biomarkers disclosed herein. For example, a biomarker panel can include one or more bacteria, one or more clinical parameters, one or more polypeptides present in the gut, or any combination thereof.

A gut bacterium biomarker for predicting treatment outcome (e.g., response to primary CDI treatment) in a mammal (e.g., a human) having CDI can be, for example, *Ruminococcaceae, Rikenellaceae, Clostridiaceae, Bacteroides, Faecalibacterium,* or *Rothia*. In some cases, one or more gut bacterial biomarkers for predicting response to primary CDI treatment can be in a biomarker panel. For example, a biomarker panel for predicting treatment response to primary CDI treatment can include two or more (e.g., two, three, four, five, or six) of *Ruminococcaceae, Rikenellaceae, Clostridiaceae, Bacteroides, Faecalibacterium,* and *Rothia*. The *Faecalibacterium* can be *Faecalibacterium prausnitzii*. The *Rothia* can be *Rothia mucilaginosa*.

A gut bacterium biomarker for predicting treatment outcome (e.g., risk of recurrence after primary CDI treatment) in a mammal (e.g., a human) having CDI can be, for example, a *Veillonella, Enterobacteriaceae, Streptococcus, Parabacteroides,* or *Lachnospiraceae*. In some cases, one or more gut bacterial biomarkers for predicting risk of recurrence after primary CDI treatment can be in a biomarker panel. For example, a biomarker panel for predicting treatment response can include two or more (e.g., two, three, four, or five) of *Veillonella, Enterobacteriaceae, Streptococcus, Parabacteroides,* and *Lachnospiraceae*. The *Enterobacteriaceae* can be *Enterobacteriaceae erwinia*. The *Veil-*

*lonella* can be *Veillonella dispar* or *Veillonella parvula*. The *Parabacteroides* can be *Parabacteroides distasonis*.

A clinical parameter biomarker for predicting treatment outcome (e.g., response to primary CDI treatment and/or risk of recurrence after primary CDI treatment) in a mammal (e.g., a human) having CDI can be, for example, severity of CDI, prior antibiotic use (e.g., β-lactam antibiotics such as cephalosporins, penicillins such as amoxicillin, and/or floroquinolones such as ciprofloxacin), the mode of *C. difficile* acquisition (e.g., community acquired *C. difficile* or hospital acquired *C. difficile*), prior antineoplastic use (e.g., methotrexate and paclitaxel), prior proton pump inhibitor (PPI) use (e.g., omeprazole, lansoprazole, dexlansoprazole, esomeprazole, pantoprazole, rabeprazole, and ilaprazole), and combinations thereof. In some cases, one or more clinical parameters for predicting response to primary CDI treatment can be in a biomarker panel. For example, a biomarker panel for predicting treatment response to primary CDI treatment can include two or more of severity of CDI, prior antibiotic use, and mode of *C. difficile* acquisition.

A polypeptide biomarker (e.g., an enzyme produced by a bacterium present in the gut) for predicting treatment outcome (e.g., response to primary CDI treatment and/or risk of recurrence after primary CDI treatment) in a mammal (e.g., a human) having CDI can be, for example, a polypeptide can be a carbohydrate-active enzyme. Non-limiting examples of carbohydrate-active enzymes include polysialyltransferases (e.g., GT38), dextransucrases (e.g., GH70), α-mannosidases (e.g., GH38), β-galactosidases (e.g., GH59), and carbohydrate-binding modules (e.g., CBM16, CBM42). In some cases, one or more (e.g., two, three, four, five, six, seven, eight, nine, ten, or more) polypeptides for predicting risk of CDI recurrence after primary CDI treatment can be in a biomarker panel. For example, a biomarker panel for predicting risk of recurrence after primary CDI treatment can include two or more of GT38, GH70, GH38, GH59, CBM16, and CBM42.

A polypeptide biomarker for predicting treatment outcome (e.g., response to primary CDI treatment and/or risk of recurrence after primary CDI treatment) in a mammal (e.g., a human) having CDI can be, for example, a carbohydrate-active enzyme. Non-limiting examples of carbohydrate-active enzymes include β-fucosidases (e.g., GT30), and carbohydrate-binding modules (e.g., CBM20). In some cases, one or more (e.g., two, three, four, five, six, seven, eight, nine, ten, or more) polypeptides for predicting risk of CDI recurrence after primary CDI treatment can be in a biomarker panel. For example, a biomarker panel for predicting risk of recurrence after primary CDI treatment can include at least one of GT30 and CBM20.

One or more gut microbiota biomarkers described herein and/or one or more polypeptides present in the gut described herein can be detected in a biological sample (e.g., a fecal sample) using any suitable technology. Methods of detecting a bacterium can include, for example, identification of operational taxonomic units and 16s sequencing. In some cases, detecting a bacterium can also include isolation of DNA from the biological sample (e.g., a fecal sample). Methods of detecting a polypeptide can include, for example, immunoprecipitation, electrophoresis, western blot, spectrophotometry, and enzyme assay.

One or more clinical parameter biomarkers described herein can be detected by any suitable method. Methods of detecting a clinical parameter can include, for example, reviewing a medical record (e.g., an electronic medical record or a physical medical record), obtaining information by word of mouth (e.g., from a clinician or from the patient), and by clinical testing for the parameter.

Detection of one or more biomarkers described herein can be used to predict a response to primary CDI treatment in a mammal having CDI. For example, a mammal can be identified as being likely to respond to primary CDI treatment if one or more (e.g., two or more, three or more, four or more, five or more, etc.) biomarkers described herein are altered (e.g., increased or decreased) or identified relative to a control biomarker panel. As used herein, a response to primary CDI treatment means a mammal may show a reduction or resolution in CDI symptoms within 4-5 days of primary CDI treatment. In some cases, a mammal can be identified as being likely to response to primary CDI treatment if one or more (e.g., two or more, three or more, four or more, or five or more) of *Ruminococcaceae, Rikenellaceae, Clostridiaceae, Bacteroides, Faecalibacterium* (e.g., *Faecalibacterium prausnitzii*), and *Rothia* (e.g., *Rothia mucilaginosa*) are increased. In some cases, a mammal can be identified as being likely to response to primary CDI treatment if the mammal is identified with community acquired *C. difficile*. In some cases, mammal can be identified as being likely to respond to primary CDI treatment if one or more (e.g., two or more) of GT38, GH70, and GH38 are increased and one or more (e.g., two or more) of GH59, CBM16, and CBM42 are decreased. For example, a mammal can be identified as being likely to have primary CDI treatment failure if one or more (e.g., two or more, three or more, four or more, five or more, etc.) biomarkers described herein are altered (e.g., increased or decreased) or identified relative to a control biomarker panel. As used herein, failure to respond to primary CDI treatment means a mammal may show no reduction in CDI symptoms within 4-5 days of primary CDI treatment. In some cases, a mammal can be identified as being likely to have primary CDI treatment failure if the mammal is identified with one or more (e.g., two or more, or three or more) of severe CDI, prior antibiotic use (e.g., β-lactam antibiotics such as cephalosporins, penicillins such as amoxicillin, and/or floroquinolones such as ciprofloxacin), and hospital-acquired *C. difficile*.

Detection of one or more biomarkers described herein can be used to predict risk of recurrence after primary CDI treatment in a mammal having CDI. For example, a mammal can be identified as being at risk of recurrence after primary CDI treatment if one or more (e.g., two or more, three or more, four or more, five or more, etc.) biomarkers described herein are altered (e.g., increased or decreased) or identified relative to a control biomarker panel. As used herein, recurrence after primary CDI treatment means a mammal may show recurrence of CDI symptoms (e.g., diarrhea) after reduction or resolution of symptoms at any time during the primary CDI treatment or within about 30 to 75 days (e.g., within 35 to 70 days, within 40 to 65 days, within 45 to 60 days, within 50 to 55 days of the primary CDI treatment) of CDI onset. In some cases, a mammal can be identified as being at risk of recurrence if one or more (e.g., two or more, three or more, or four or more) of *Veillonella* (e.g., *Veillonella dispar* or *Veillonella parvula*), *Enterobacteriaceae* (e.g., *Enterobacteriaceae enwinia*), *Streptococcus*, *Parabacteroides*, and *Lachnospiraceae* are increased. In some cases, a mammal can be identified as being at risk of recurrence if the mammal is identified with one or more (e.g., two or more, three or more, or four or more) of increasing age, prior antibiotic (e.g., metronidazole and/or vancomycin) use, decreased anti-toxin IgG levels, the presence of comorbidities, and use of gastric acid suppression medications. In some cases, a mammal can be identified as being at risk of recurrence if one or more of GT30 and CBM20 are increased.

Once identified as being likely to respond to primary CDI treatment, a mammal can be treated for CDI. For example, a mammal identified as being likely to respond to primary CDI treatment can be treated by, for example, administering one or more primary CDI therapies. Non-limiting examples of primary CDI therapies include oral delivery of antimicrobials (e.g., metronidazole, vancomycin, fidaxomicin, and combinations thereof.

Once identified as being at risk of CDI recurrence after primary CDI treatment, a mammal can be treated for CDI. For example, a mammal identified as being at risk of CDI recurrence after primary CDI treatment can be treated by, for example, administering one or more advanced CDI therapies. Non-limiting examples of advanced CDI therapies include pulsed antimicrobial regimens, fecal microbiota transplantation, defined microbial consortia, surgery (e.g., to remove diseased portions of the colon), and combinations thereof.

The invention will be further described in the following examples, which do not limit the scope of the invention described in the claims.

EXAMPLES

Example 1: Study Design

Patients with a first *Clostridium difficile* infection (CDI) episode were recruited. Consecutive patient stool samples that led to CDI diagnosis were collected.

Clinical data including demographics, hospitalization, concomitant medications, severity, laboratory parameters, prior and concomitant antibiotic use, initial CDI treatment, treatment response and recurrent CDI were obtained by a review of the electronic medical record.

CDI was defined as community-acquired if onset of symptoms occurred in the community or within 48 hours of admission to a hospital, provided symptom onset was >12 weeks after the last discharge from a hospital. CDI was defined as hospital acquired if onset of symptoms occurred after 48 hours of admission to a hospital or within 4 weeks of last hospital discharge.

CDI was considered indeterminate if symptom onset occurred between 4 and 12 weeks after a hospital dismissal (Khanna et al., 2012 *Am J Gastroenterol* 107:89-95; and Cohen et al., 2010 *Infect Control Hosp Epidemiol* 31:431-55). Severe CDI was defined as a peripheral white blood cell count ≥15,000 cells/mm3 or a serum creatinine rise of ≥50% from baseline within 7 days of diagnosis. CDI was classified as severe-complicated if the infection was complicated by sepsis, hypotension, ileus, toxic megacolon, perforation, need for intensive care unit admission, surgery for a CDI-related complication (e.g., megacolon, perforation, refractory colitis), or death (Cohen et al., 2010 *Infect Control Hosp Epidemiol* 31:431-55).

Treatment failure was defined as non-response to treatment after 5 days of metronidazole treatment or 4 days of vancomycin therapy (Khanna et al., 2012 *Am J Gastroenterol* 107:89-95; Cohen et al., 2010 *Infect Control Hosp Epidemiol* 31:431-55; and Surawicz et al., 2013 *Am J Gastroenterol* 108:478-98). Recurrent CDI was defined as recurrence of diarrhea after complete resolution of symptoms at any time during the treatment or within 56 days of onset with a positive CDI test (Cohen et al., 2010 *Infect Control Hosp Epidemiol* 31:431-55).

Stool samples were processed for next generation sequencing as described below and changes in microbial community structure and function were correlated to treatment response and risk of recurrence.

Example 2: Sequencing and Analytic Methods 16S sequencing data processing. Fecal samples were kept frozen at −80° C. until they were processed. After fecal DNA isolation (MoBio, Carlsbad, Calif. fecal DNA kit), amplicons spanning the variable region 4 of bacterial 16S rRNA were generated and sequenced using illumina Mi Seq platform. The 16S rRNA sequencing data from the illumina runs were trimmed, demultiplexed, chimera filtered and assigned to operational taxonomic units (OTUs) using packages implemented in Quantitative Insights Into Microbial Ecology (QIIME) 1.8.0 software (Caporaso et al., 2010 *Nat Methods* 7:335-6). Closed reference OTU assignment was performed using 'uclust' with a 97% sequence similarity threshold against the Greengenes 13.8 database as a reference (DeSantis et al., 2006 *Appl Environ Microbiol* 72:5069-72).

Data Analyses.

Built-in functions of the QIIME pipeline were applied. Alpha diversity metrics were computed using non-phylogeny based metrics (Observed species, Chao1 index, Shannon index) and phylogeny-based metrics (Phylogenetic Distance whole tree). Differences between fecal samples from responders and non-responders or from patients with or without recurrence after initial response, were tested for differences with a Monte Carlo permuted t-test. Beta diversity metrics were computed using unweighted and weighted UniFrac distances and visualized with Principal Coordinate Analysis (PCoA) (Lozupone et al., 2011 *ISME J* 5:169-72). The differences between fecal samples from responders and non-responders or from patients with or without recurrence after initial response were treated with the Permutational Multivariate Analysis of Variance Using Distance Matrices (PERMANOVA) method (Anderson, 2001 *Austral Ecology* 26:32-46).

Comparisons of relative abundance of taxa between responders and non-responders, or between patients with and without recurrence after initial response, was performed using Linear discriminant analysis Effect Size (LEfSe), a non-parametric Mann-Whitney U test applied to detect features with significant differential abundance with respect to the groups compared, followed by a Linear Discriminant Analysis (LDA) to estimate the effect size of each differentially abundant feature (Segata et al., 2011 *Genome Biol* 12:R60). A LDA score (log 10) >2 was considered significant.

A risk index was built to differentiate responders from non-responders to initial treatment or patients with and without recurrence after initial response, based on taxonomy. A non-collapsed OTU table was used. All the taxa with a LDA score (log 10) >2 were included in the calculation of the risk index. In order to build the risk index to predict the patients who would respond or not respond to treatment, the relative abundances (arcsine square root transformed) of the taxa associated with the responders to treatment (based on the LEfSe output on the OTU table) were summed and the relative abundances of the taxa associated with non-responders to treatment (based on the LEfSe output) were summed. Then the difference between these two sums (relative abundance of the taxa associated with no response to treatment minus relative abundance of the taxa associated with response to treatment) was calculated, thereby obtaining a risk index. This procedure was repeated n (overall sample size) times to obtain a risk index for each patient in the cohort.

A leave-one-out cross-validation procedure was also conducted to evaluate the taxa that differentiated patients with or without response to treatment in the held-out patient, based on the LEfSe output of n−1 patients. The taxa that differentiated patients with or without response to treatment were identified using LEfSe in the n−1 dataset. Then, the relative abundances of the taxa associated with response to treatment (based on the LEfSe output of the n−1 dataset) were identified and the relative abundances of taxa associated with no response to treatment (based on the LEfSe output of the n−1 dataset) on the held-out patient summed. Then the difference between these two sums (relative abundance of taxa associated with no response to treatment minus relative abundance of taxa associated with response to treatment) was calculated and a risk index obtained for the held-out patient. The procedure was repeated n times to produce a risk index in each of the held-out patients based on the difference between the sum of the taxa associated with the no response to treatment minus the sum of the taxa associated with response to treatment found in each of the n−1 datasets. The significance of the difference in risk indexes between the patients with response to treatment and patients without response to treatment was assessed using a permutation test, in which we permuted the labels of the outcome (that is response or non-response to treatment) 999 times, each time deriving new held-out predictions of the risk indexes for each subject for that outcome. The two procedures (creation of a risk index and leave-one-out cross-validation) were applied in the exact same way to compare patients with recurrence or no recurrence after initial response to treatment.

Receiving operating characteristic (ROC) curves were plotted and the area under the curve (AUC) values were computed on a dataset containing 10 sets of predictions and corresponding labels obtained from 10-fold cross-validation using ROCR package in R (Sing et al., 2005 Bioinformatics 21:3940-1; R Development Core Team 2011 ISBN: 3-900051-07-0). A risk index threshold was also determined that best predicted response or no-response to treatment, or recurrence after initial response to treatment, with a leave-one-out cross-validation on the produced risk indexes from each patient. A ROC curve that included risk indexes from n−1 patients was built. The cutoff associated with a given specificity was determined. This cutoff was used to determine the outcome of the held-out patient. Thus, each held-out sample was treated as a new patient on whom the optimal risk index cutoff was tested to separate patients who respond to treatment and patient who did not respond to treatment. This procedure was repeated n times and we calculated the accuracy of the cutoff by summarizing the good prediction of the outcome of each held-out patient. Boxplots, beeswarms and two-dimensional PCoA plots were generated using R (R Development Core Team 2011 ISBN: 3-900051-07-0).

Network analyses were displayed with Cytoscape using an edge-weighted spring embedded layout (Smoot et al., 2011 Bioinformatics 27:431-2). OTUs were collapsed to the genus level to eliminate OTUs present in fewer than 25% of samples. Genera present in less than 25% of the samples were removed to reduce the very large number of multiple hypotheses tested in correlation network analysis. Spearman correlation of taxon-taxon relative abundance was performed and included only those links with absolute value of correlation >0.5 and False Discovery Rate (FDR)-corrected p-value <0.05.

Example 3: Clinical Characteristics Predict Response CDI Therapy and CDI Recurrence Stool samples were collected from 88 patients (median age 52.7 years, interquartile range 36.9-65.1; 60.2% female) and clinical outcomes were recorded prospectively. The rate of primary non-response following recommended treatment was 12.5%, and was similar between metronidazole and vancomycin (Table 1).

In order to identify clinical characteristics that predict response to treatment in CDI, chi-square and univariate analyses were performed. There were no significant differences in age, sex, body-mass index, treatment regimen and concomitant systemic antibiotic exposure in primary non-responders compared to responders (Table 1). There were non-significant trends in prior antibiotic exposure, acquisition mode age, and severity of CDI in primary non-responders compared to responders (Table 1).

TABLE 1

Clinical characteristics of all patients

|  | Overall (n = 88) | Treatment responder (n = 77) | Treatment failure (n = 11) | p-value* | Treatment success with no recurrence (n = 55) | Treatment success with recurrence (n = 22) | p-value** |
|---|---|---|---|---|---|---|---|
| Age (median) | 52.7 | 53.8 | 49.9 | 0.67 | 55.6 | 49.0 | 0.62 |
| Sex (% female) | 60.2 | 59.7 | 63.6 | 0.8 | 58.2 | 63.6 | 0.65 |
| BMI, mean (Kg/M$^2$) | 27.5 | 27.4 | 28.1 | 0.75 | 27.7 | 26.6 | 0.44 |
| Prior antibiotic exposure (%) | 59 | 55.8 | 81.8 | 0.1 | 56.4 | 54.5 | 0.88 |
| Community-acquired (%) | 59.1 | 62.3 | 36.4 | 0.13 | 63.6 | 59.1 | 0.9 |
| Severe CDI (%) | 7 | 5.2 | 18.2 | 0.1 | 5.5 | 4.5 | 0.86 |
| Concomitant antibiotic exposure (%) | 28.4 | 27.2 | 36.4 | 0.5 | 27.3 | 27.3 | 1.0 |
| Concomitant PPI exposure (%) | 27.3 | 25.9 | 36.3 | 0.48 | 18.2 | 45.5 | 0.01 |

TABLE 1-continued

Clinical characteristics of all patients

|  | Overall (n = 88) | Treatment responder (n = 77) | Treatment failure (n = 11) | p-value* | Treatment success with no recurrence (n = 55) | Treatment success with recurrence (n = 22) | p-value** |
| --- | --- | --- | --- | --- | --- | --- | --- |
| Treatment with metronidazole (%) | 70.5 | 70.1 | 72.7 | 0.8 | 72.7 | 63.6 | 0.1 |
| Treatment with vancomycin (%) | 23.9 | 24.7 | 18.2 | 0.8 | 20.0 | 36.4 | 0.1 |
| Treatment with vancomycin and metronidazole | 5.6 | 5.2 | 9.1 | 0.8 | 7.3 | 0 | 0.1 |
| Treatment failure (%) | 12.5 | — | — | — | — | — | — |
| Recurrence after successful treatment (%) | — | 28.5 | — | — | — | — | — |

*Denotes p-value for comparison of treatment responders versus treatment failures
**Denotes p-value for comparison of recurrent infections versus non-recurrent infection
CDI = *Clostridium difficile* infection, BMI = Body mass index These results demonstrate that clinical parameters of prior antibiotic exposure, community-acquired CDI, and/or severe CDI can predict patient response to primary CDI treatment.

Example 4: Gut Microbiota Signatures can Predict CDI Response to Therapy

Of the 88 fecal samples collected, a total of 1,449,211 high-quality 16S rRNA gene-encoding sequences were identified, representing 7,470 OTUs. The mean number of sequences obtained per sample was 16,468±4,674. Since samples contained between 6,987 and 35,494 sequences, diversity analyses were rarefied at 6,987 sequences per sample to avoid bias.

A panel of 36 OTUs that were significantly different between primary non-responders and responders was identified using LEfSe (significance corresponding to a LDA ($\log_{10}$)>2). Patients with successful response to treatment had a significant increase in OTUs within *Ruminococcaceae*, *Rikenellaceae*, *Bacteroides* species, *Faecalibacterium prausnitzii*, while primary non-responders had a significant increase in *Clostridiaceae*, *Lachnospiraceae*, *Blautia* species, *Coprococcus*, *Clostridium* species, *Clostridium perfringens*, *Streptococcus* species, *Bifidobacterium*, *Ruminococcus gnavus* and *Actinomyces* species (FIG. 1).

Figure 2:
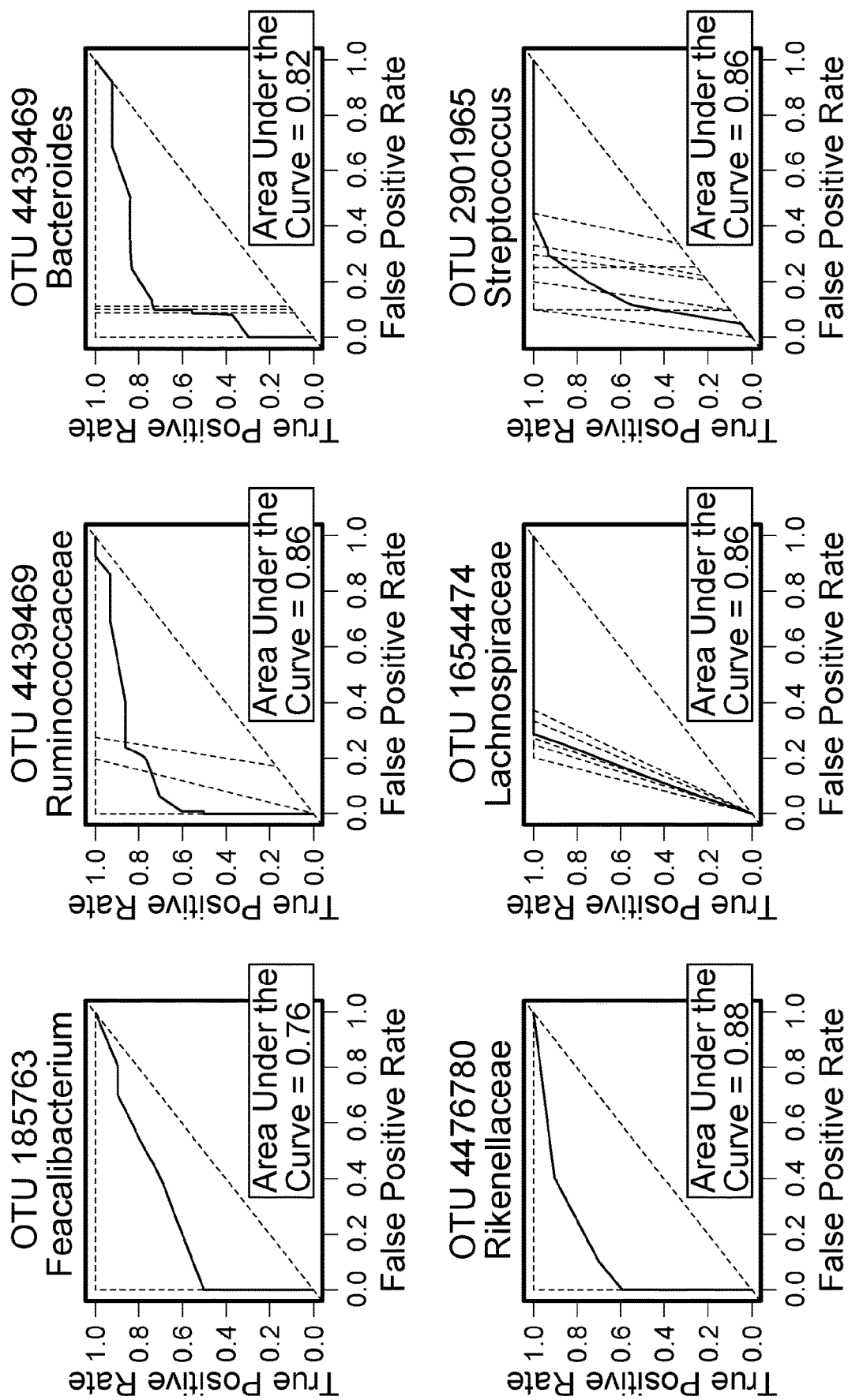
FIG. 2 shows a receiver operating characteristic (ROC) curve analysis of the most distinctive Operational taxonomic units in fecal samples collected prior to treatment following 10-fold jack-knifing. The 10 ROC curves are in blue and the mean ROC curve is depicted in black.
Figure 2:
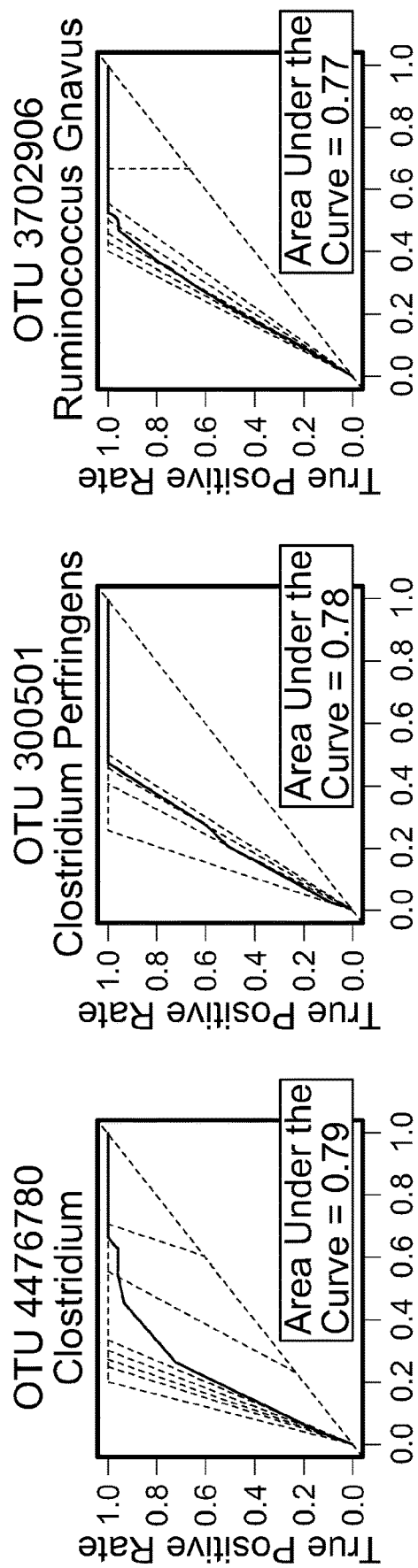
Figure 3A:
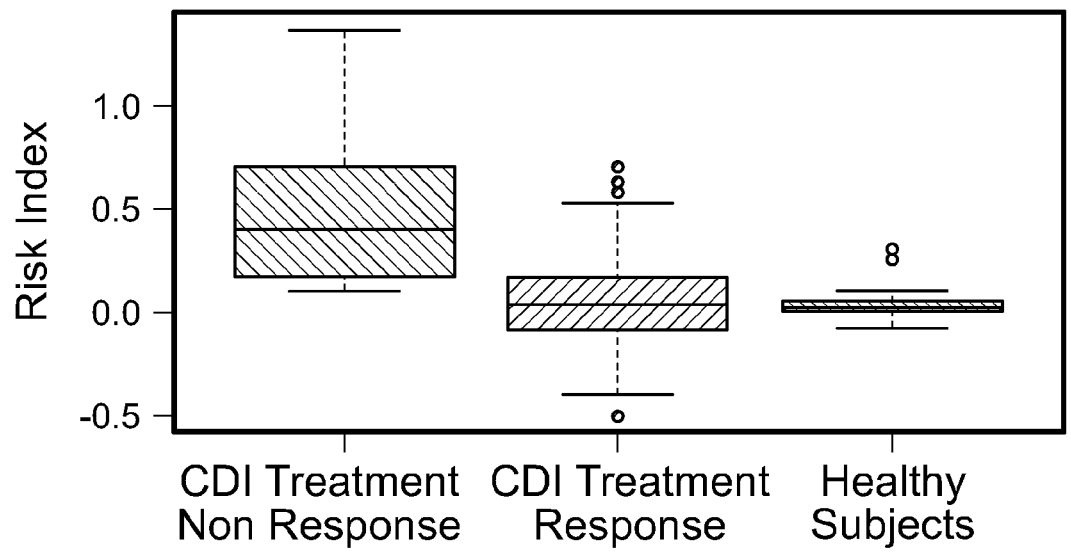
FIGS. 3 A-C show a risk index of non-response to treatment from this panel of OTUs that were significantly different between responders and non-responders. (A) CDI risk index based on the differentiated operational taxonomic units in non-responders, responders, and healthy controls calculated using the Mann-Whitney U test: ***: $p<0.001$. The boxplots denote top quartile, median and bottom quartile and individual dots represent individual patient samples. (B) ROC curve analysis of the CDI risk index in pre-treatment fecal samples collected following 10-fold cross-validation (left graph), and ROC curve analysis of the CDI risk index in pre-treatment fecal samples collected following 10-fold cross-validation of all the held-out samples from the leave-one-out cross-validation analysis (right graph). Following the leave-one-out procedure, the ROC curves of each leave-one-out procedure are in blue and the mean ROC curve of all the procedure is in black. (C) Beeswarm plot of all the held-out samples from the leave-one-out (LOO) cross-validation ($p<0.0001$).
Figure 3B:
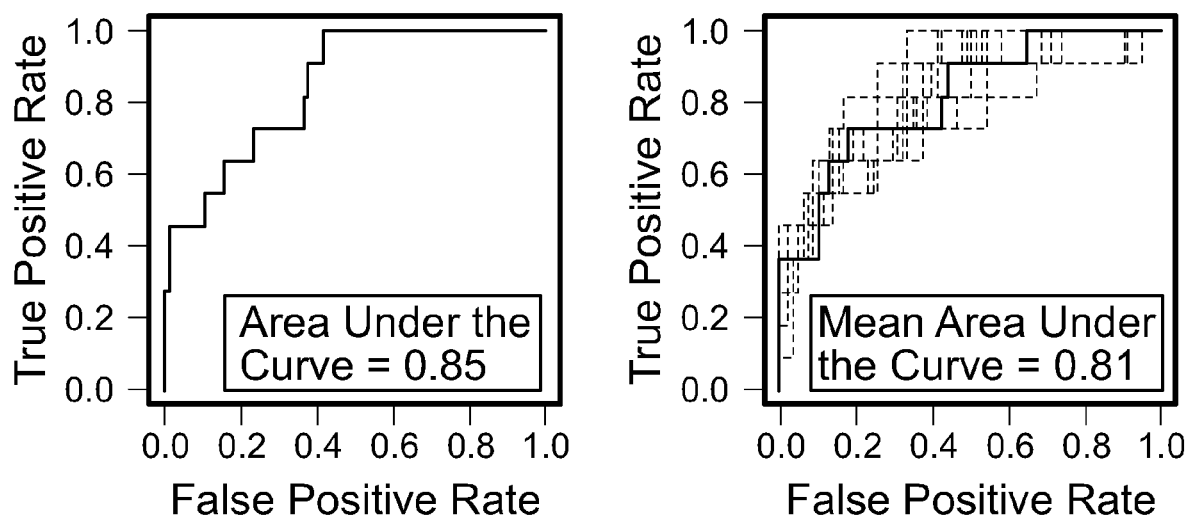

The ability of this panel of microbes to discriminate between responders and non-responders was tested using jackknifed ROC curve analysis and found several individual OTUs to be strong predictors of response to treatment (FIG. 2). Several individual OTUs were found to be strong predictors of response. *Faecalibacterium* species yielded a ROC-plot AUC value of 0.76, *Ruminococcaceae* yielded a ROC-plot AUC value of 0.86, *Bacteroides* species yielded a ROC-plot AUC value of 0.82, *Rikenellaceae* yielded a ROC-plot AUC value of 0.88, *Lachnospiraceae* yielded a ROC-plot AUC value of 0.86, *Streptococcus* species yielded a ROC-plot AUC value of 0.86, *Clostridium* species yielded a ROC-plot AUC value of 0.79, *Clostridium perfringens* yielded a ROC-plot AUC value of 0.78 and *Ruminococcus gnavus* yielded a ROC-plot AUC value of 0.77. A risk index of non-response to treatment was built from this panel of OTUs that were significantly different between responders and non-responders. This risk index, calculated in each patient (responders and non-responders), corresponds to the difference between the sum of the relative abundance of all the OTUs associated with non-response to treatment and the sum the relative abundance of the OTUs associated with responses to treatment. This risk index was significantly different in the two groups of patients, with a mean score of 0.07±0.24 in responders and 0.42±0.52 in non-responders (Mann-Whitney U test, p=0.0002) (FIG. 3A). Moreover, the ROC curve analysis showed that this risk index was a strong predictor of treatment response, with an area under the curve of 0.85 (FIG. 3B).

Figure 3C:
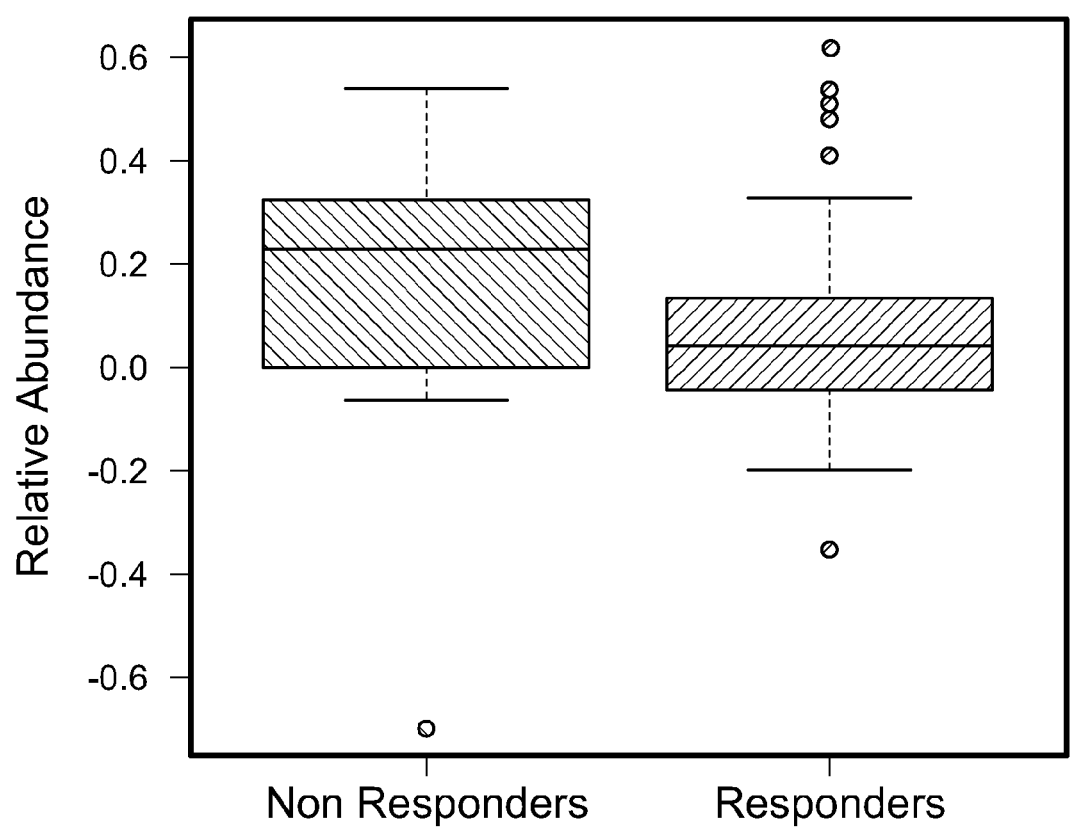

In order to determine the risk index threshold that best predicts response to treatment the leave-one-out cross-validation was used on our risk index. Each held-out patient was treated as a new patient, independently from the initial cohort, on whom we tested and subsequently refined the optimal index cut-off to separate responders and non-responders. This LOO cross-validation procedure demonstrated that the sensitivity of a risk index threshold of 0.23 was 75% to predict the response to treatment in a new patient, at a specificity of 70%. Furthermore, another LOO procedure, where the risk index was built 88 times using n−1 samples each time and then tested on the held-out sample, showed the gut microbiota profile to be a strong predictor of response vs. non-response (permutation test; p<0.0001; FIG. 3C).

OTU Networks are Disrupted in Primary Non-Responders.

Figure 4A:
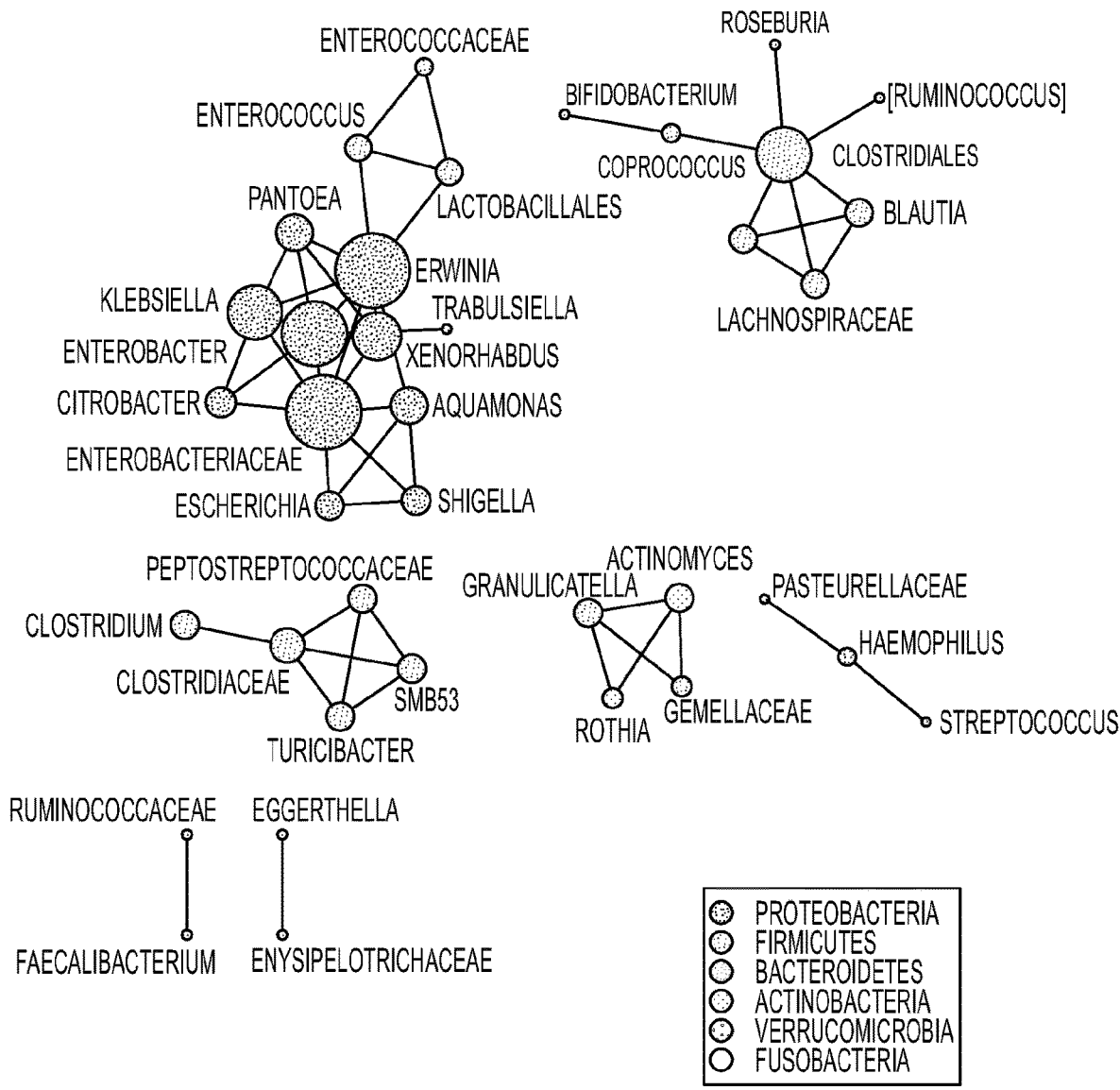
FIGS. 4 A-B show Spearman correlations demonstrating taxon-taxon relative abundance including links with absolute value of correlation $>0.5$ and False Discovery Rate-corrected p-value $<0.05$. Network analyses displayed with Cytoscape using an edge-weighted spring embedded layout in responders (A) and non-responders (B). Positive correlations were in blue and the size of the edge is based on the strength of the correlation. The size of the node was based on the number of correlations associated with the corresponding taxon. The color of the node is based on the phylum level: Actinobacteria (blue), Bacteroidetes (green), Firmicutes (purple), Proteobacteria (yellow), Fusobacteria (pink) and Verrucomicrobia (grey). There is a three-fold decrease in the number of taxon correlations in the non-responders and most of the decreased nodes were Firmicutes and Actinobacteria.
Figure 4B:
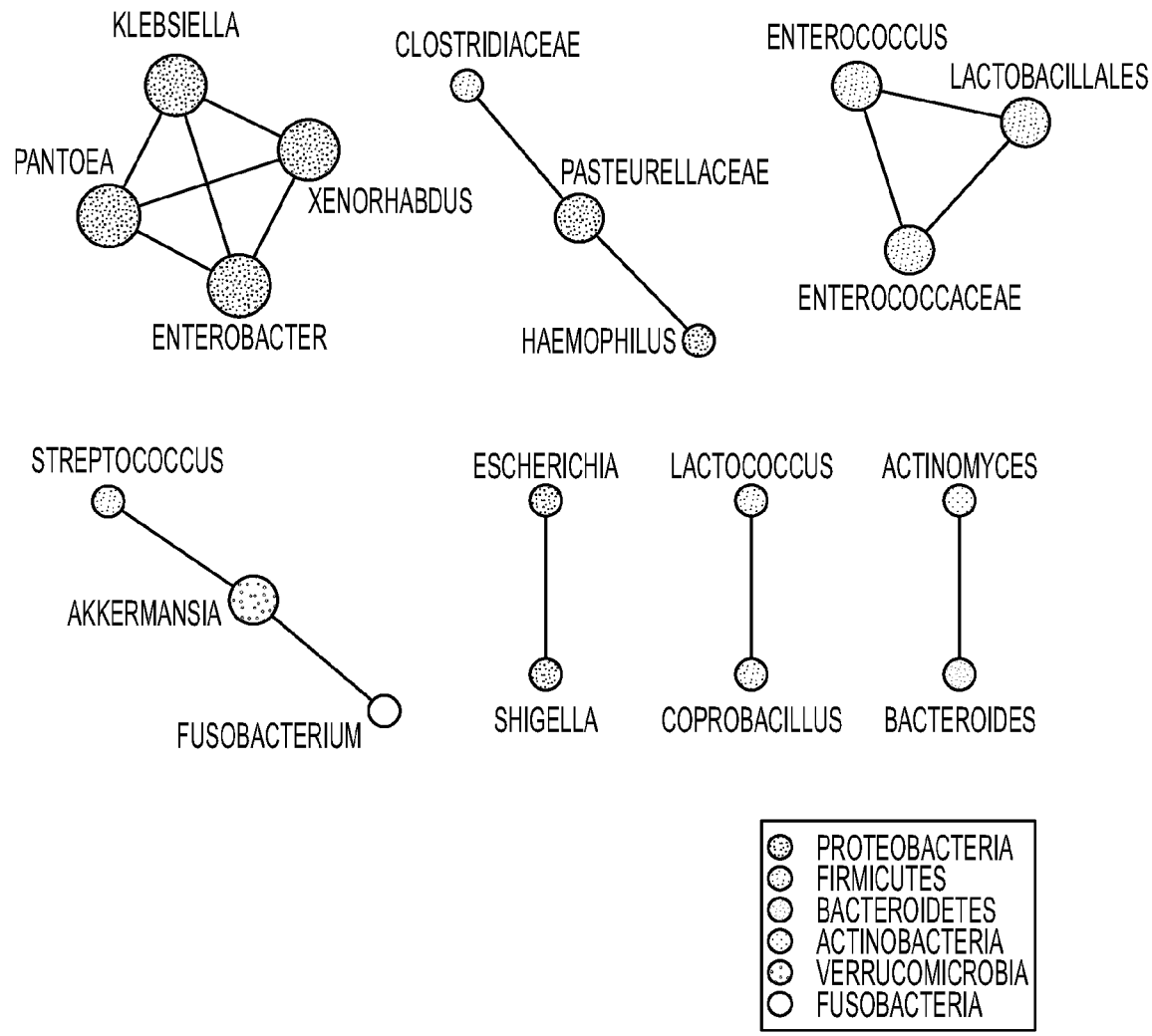

Computed OTU networks at the genus level were computed to differentiate responders and non-responders. There was a three-fold (56 versus 16, ratio=3.35) decrease in the number of strong taxon-taxon correlations (absolute value of correlation >0.5 and FDR-corrected p-value <0.05) in non-responders compared to responders, and most of the decreased nodes between responders and non-responders were members of the phylum Firmicutes (50 versus 10, ratio=5) and Actinobacteria (7 versus 1, ratio=7) (FIG. 4).

Figure 5A:
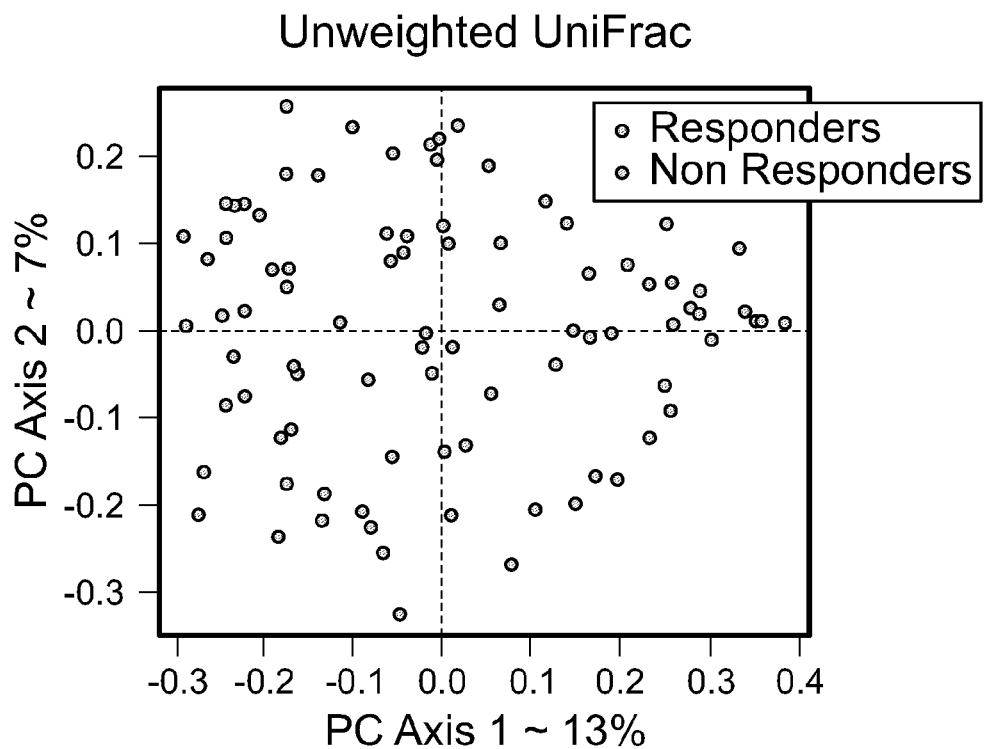
FIGS. 5 A-B show beta-diversity comparisons of the gut microbiomes of the fecal samples collected in responders and non-responders. Analyses performed on 16S rRNA V4 region data, with a rarefaction depth of 6,987 reads per sample. (A) Principal Coordinate Analysis (PCoA) of unweighted UniFrac distances. Proportion of variance explained by each principal coordinate axis is denoted in the corresponding axis label. (B) PCoA of weighted UniFrac distances. Proportion of variance explained by each principal coordinate axis is denoted in the corresponding axis label. This is no clustering between responder and non-responder samples (unweighted UniFrac distance metric: $R=-0.0888$, $p=0.980$; weighted UniFrac distance metric: $R=-0.0035$, $p=0.504$).
Figure 5B:
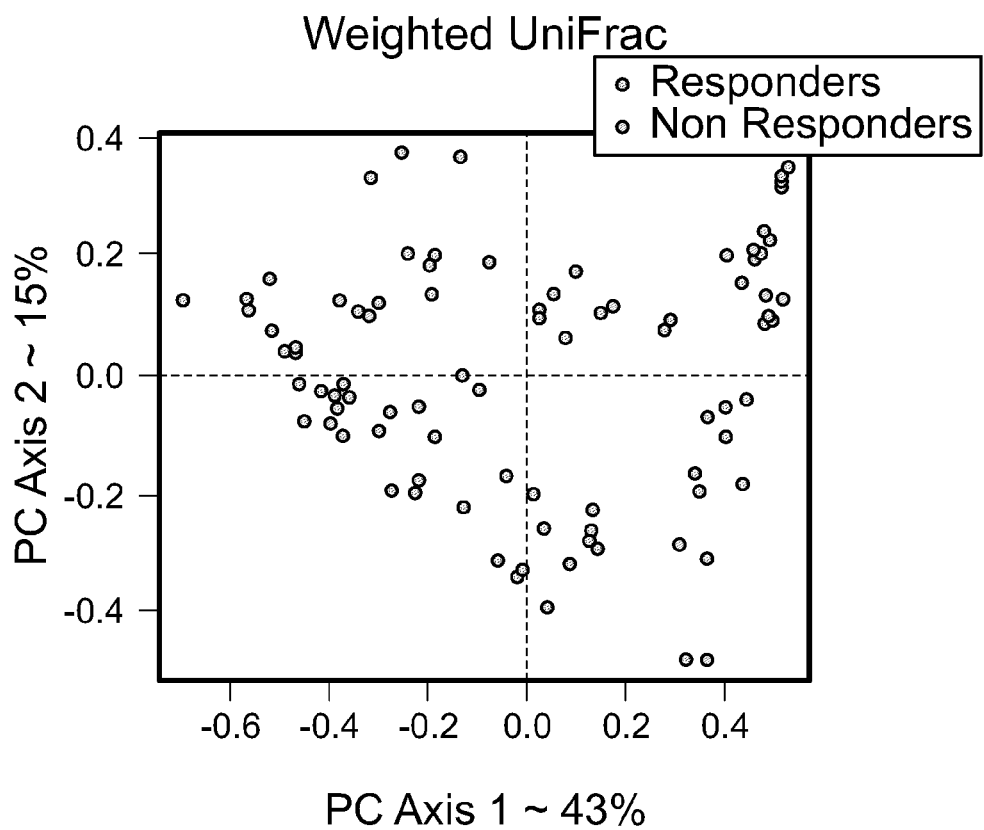
Figure 6:
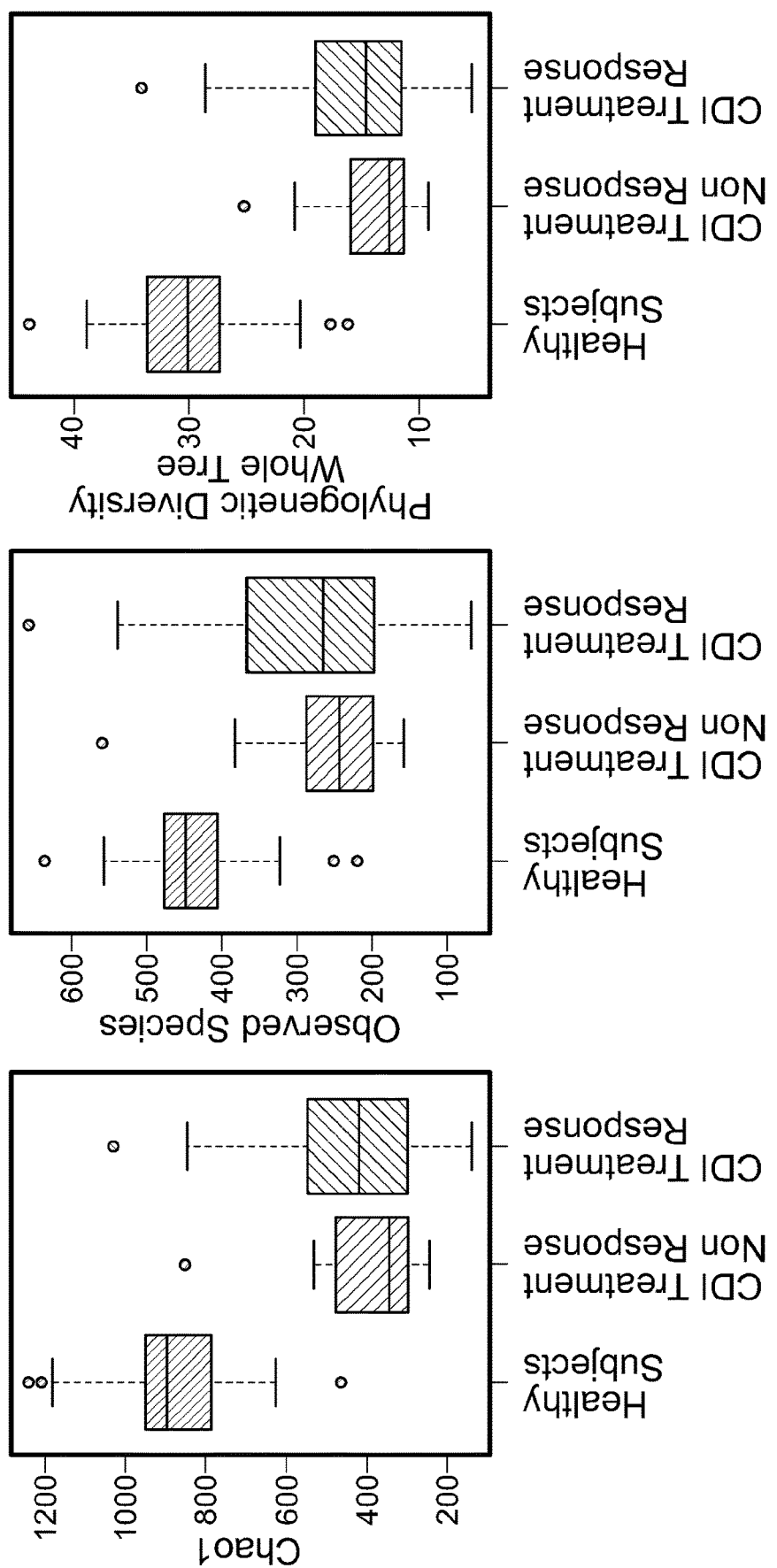
FIG. 6 shows alpha-diversity comparisons of the gut microbiomes of the fecal samples collected from responders, non-responders, and healthy subjects using both phylogenetic (Faith's phylogenetic diversity) and non-phylogenetic (observed species, Shannon index, chao 1 index) richness metrics. Analyses were performed on 16S rRNA V4 region data, with a rarefaction depth of 6,987 reads per sample. Whiskers in the boxplot represent the range of minimum and maximum alpha diversity values within a population, excluding outliers. There is a trend for alpha diversity decrease in fecal samples collected in non-responders as compared with alpha diversity from samples collected in responders, observed with both phylogenetic (Faith's phylogenetic diversity) and nonphylogenetic (observed species, Shannon index, chao 1 index) richness metrics.

Gut Microbial Diversity is not Significantly Different in Primary Non-Responders Compared to Responders Unweighted and weighted UniFrac based PCoA, based on 16S rRNA gene sequencing using MiSeq Illumina platform did not show significant differences between responders and non-responders (unweighted UniFrac distance metric:

R=−0.0888, p=0.98; weighted UniFrac distance metric: R=−0.0035, p=0.50) (FIG. 5). Similarly, although there was a trend towards decreased alpha diversity (phylogenetic diversity, observed species, shannon and chao1) in non-responders compared to responders, this difference was not significant (FIG. 6).

Gut Microbiota Functional Repertoire is Significantly Different in Responders and Non-Responders.

Figure 7:
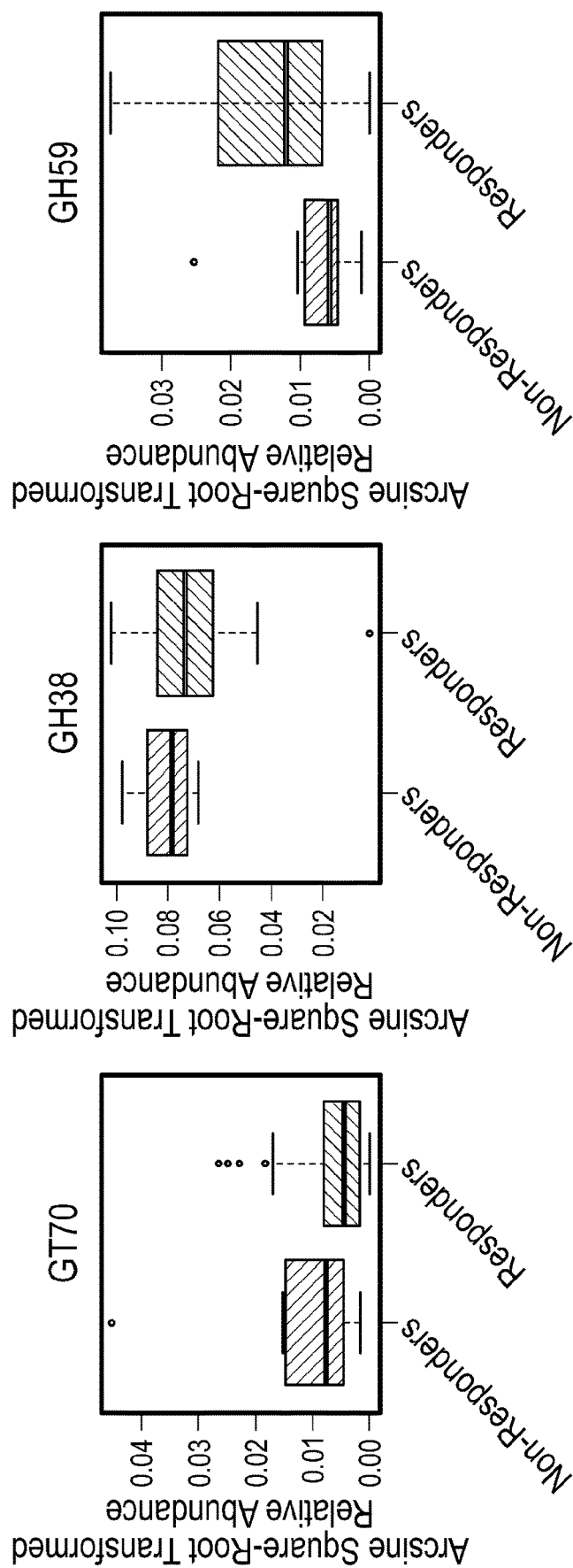
FIG. 7 shows significantly increased carbohydrate-active enzymes GH70, GT38 (dextransucrase), and GH38 (α-mannosidase); and significantly decreased GH59 (β-galactosidase) and two carbohydrate-binding modules, CBM16 and CBM42 in non-responders (n=11) compared to responders (n=77) as shown by Mann-Whitney test. Boxplots denote top quartile, median and bottom quartile.
Figure 7:
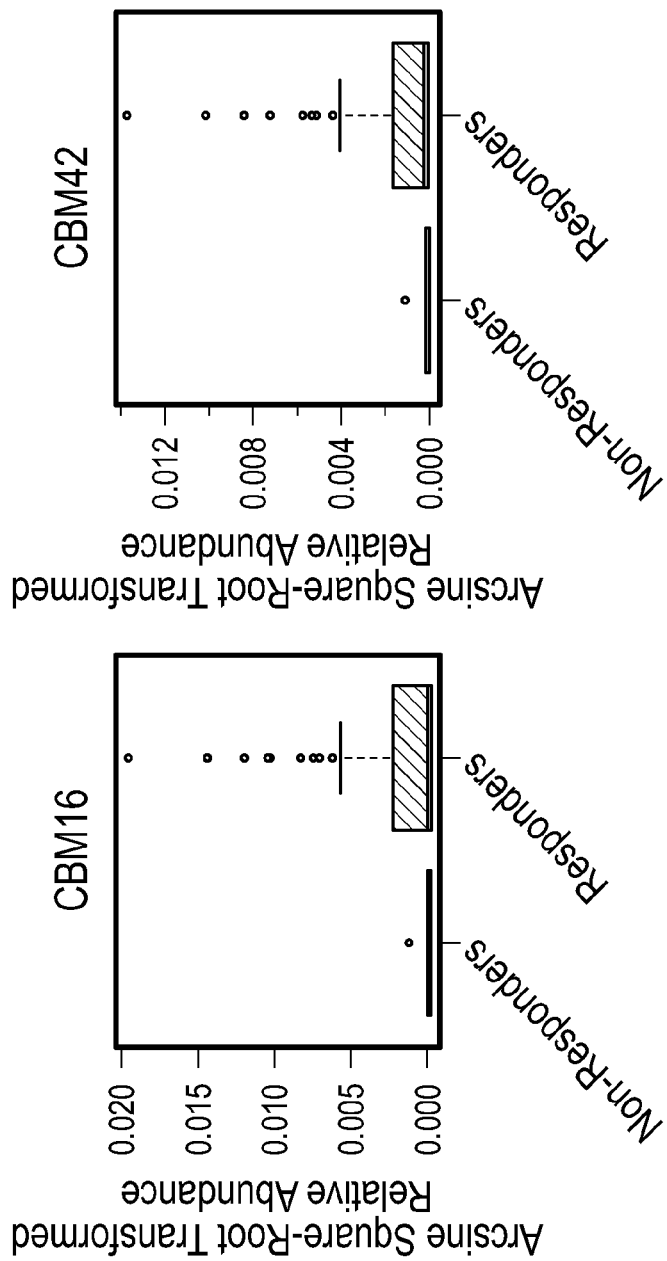

In order to determine if competition for nutritional niches in the gut may play a role in determining response to treatment by providing C. difficile with a competitive disadvantage, we used Phylogenetic Investigation of Communities by Reconstruction of Unobserved States (PICRUSt) to predict Carbohydrate-Active Enzymes database—glycoside hydrolase (CAZY GH) assignments. We used PICRUSt with defaults parameters to normalize the OTU table by dividing each OTU by the known/predicted 16S copy number abundance (normalize_by_copy_number.py script). Then, we used the precalculated file containing the CAZY GH assignments, untitled cazy_13_5_precalculated.tab, and apply the predict_metagenomes.py script as recommended, specifying CAZY GH assignments in the type of prediction. The output file gave the CAZY GH assignment in each sample included in the OTU table. Using LEfSe, we found that GT38 GH70 (dextransucrase) and GH38 (α-mannosidase) were increased whereas GH59 (β-galactosidase) and two carbohydrate-binding modules, CBM16 and CBM42 were significantly decreased in non-responders compared to responders with LDA score ($\log_{10}$) >2 (FIG. 7).

These results demonstrate that biomarkers, such as the gut microbiota signature and/or the gut microbiota functional repertoire (e.g., polypeptides present in the gut) can predict response to primary CDI treatment, differentiating responders and non-responders.

Example 5: Gut Microbiota Signature can Predict CDI Recurrence

Among the patients who initially responded to treatment, 28.5% had recurrent CDI (Table 1). There were no significant differences in age, sex, body-mass index, prior antibiotic exposure, acquisition mode, treatment regimen and concomitant systemic antibiotic exposure in patients with and without recurrent CDI (Table 1).

Figure 8:
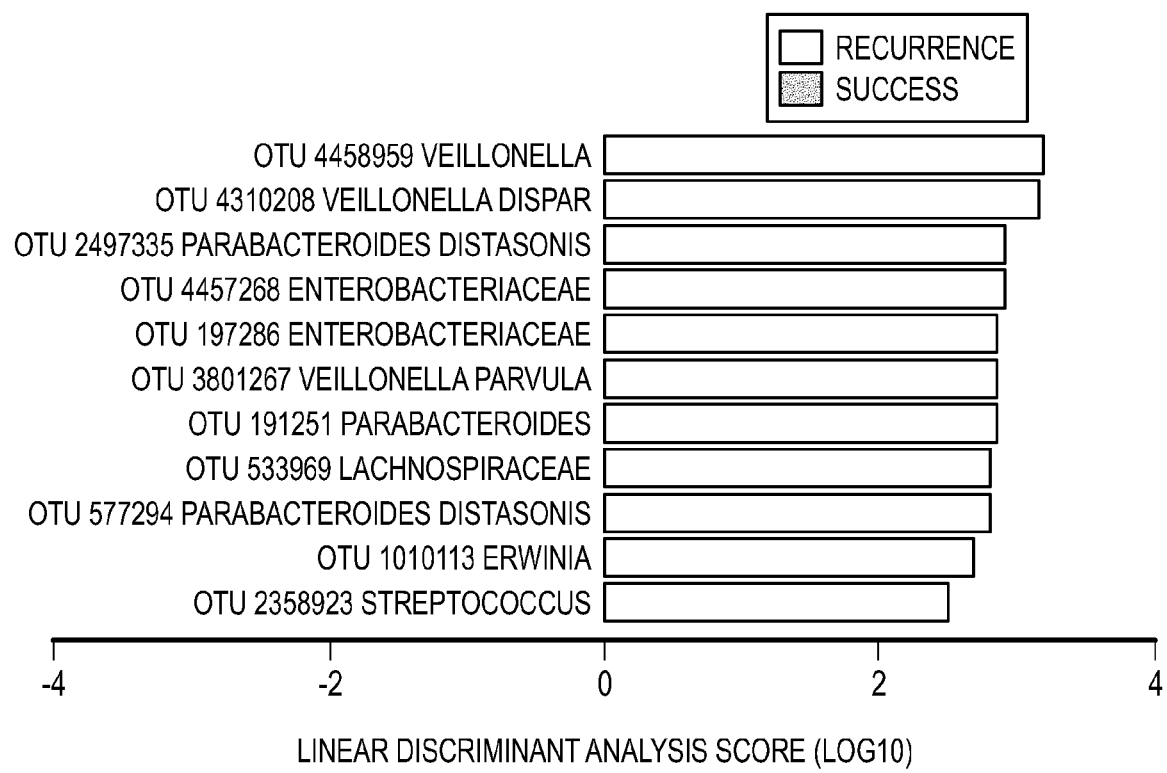
FIG. 8 shows a summary of the OTUs associated with recurrence (n=22) versus non-recurrence (n=55) after successful treatment response using Linear discriminant analysis Effect Size analysis. Representative bacteria with relative abundance of at least 1% with significant differences are represented.

A panel of 11 OTUs that were significantly different between those with (n=22) and without (n=55) recurrence following successful treatment was identified using LEfSe. Patients with recurrent CDI had a significant decrease in OTUs related to Veillonella (dispar, parvula), Enterobacteriaceae (Enwinia species), Streptococcus species, Parabacteroides distasonis and Lachnospiraceae compared to patients without recurrence (FIG. 8).

Figure 9:
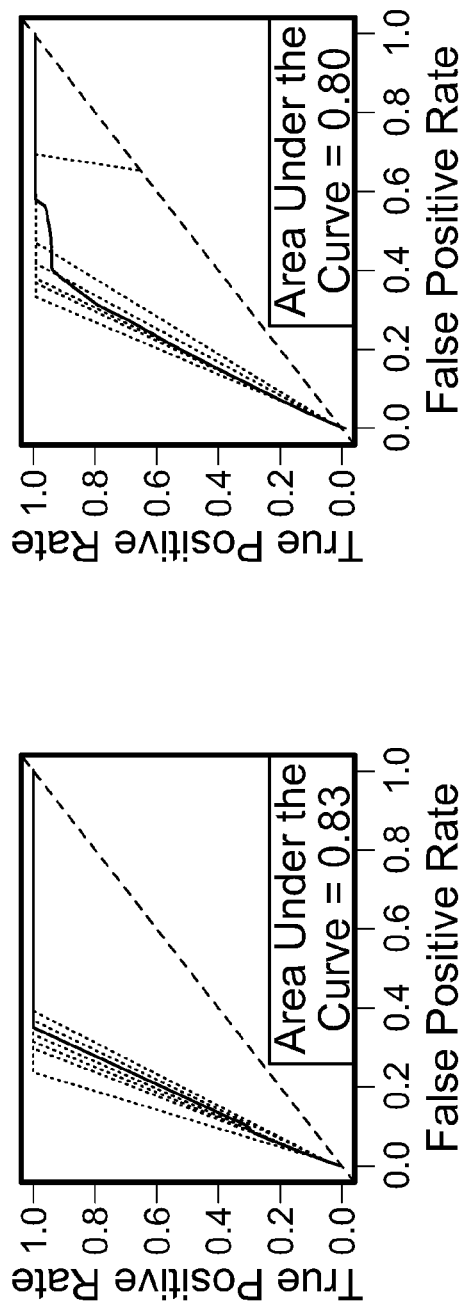
FIG. 9 shows a receiver operating characteristic analysis of the most distinctive Operational taxonomic units in fecal samples collected prior to treatment following 10-fold jack-knifing. The 10 ROC curves are in blue and the mean ROC curve is in black.

The ability of individual microbes to discriminate between patients who did or did not develop recurrent CDI was tested and several individual OTUs to be strong predictors of recurrence were found. Veillonella dispar yielded an AUC of 0.83, Veillonella parvula an AUC of 0.80, Veillonella an AUC of 0.82 and Lachnospiraceae an AUC of 0.81 (FIG. 9).

Figure 10A:
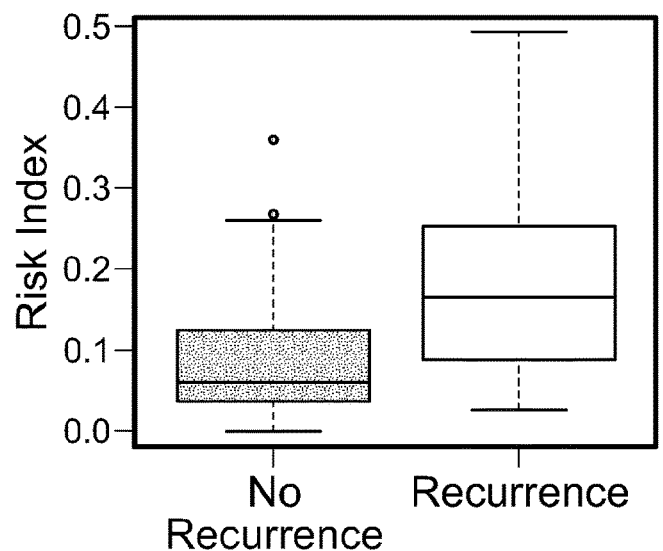
FIGS. 10 A-C show a risk index of non-response to treatment from this panel of OTUs that were significantly different between patients with and without recurrence. (A) CDI risk index based on the differentiated OTUs in patients with success versus recurrence. Mann-Whitney U test: ***: p<0.001. Boxplots denote top quartile, median and bottom quartile. (B) ROC curve analysis of the CDI risk index in fecal samples collected prior to treatment predicting recurrence. (C) ROC curve analysis of the CDI risk index in fecal samples collected prior to treatment. Following the leave-one-out procedure, the ROC curves of each leave-one-out procedure are in blue and the mean ROC curve of all the procedure is in black.
Figure 10B:
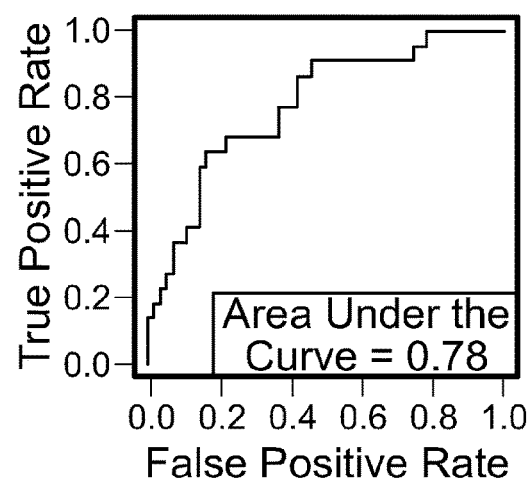

A risk index of recurrence from this panel of microbes was built which differentiated between patients with and without recurrence. This risk index included all the OTUs that had a LDA score ($\log_{10}$) >2. The risk index of recurrence is the difference between the sum of the relative abundance of the OTUs associated with recurrent CDI minus the sum of relative abundance of the OTUs associated with no recurrence. This risk index was significantly different in patients who did not have a recurrence (mean score 0.09±0.16) and those who did (0.19±0.07) (Mann-Whitney U test, p-value=0.0001) (FIG. 10A). The ROC curve analysis showed that this risk index was a strong predictor of recurrence, with an AUC of 0.85 (FIG. 10B).

Figure 10C:
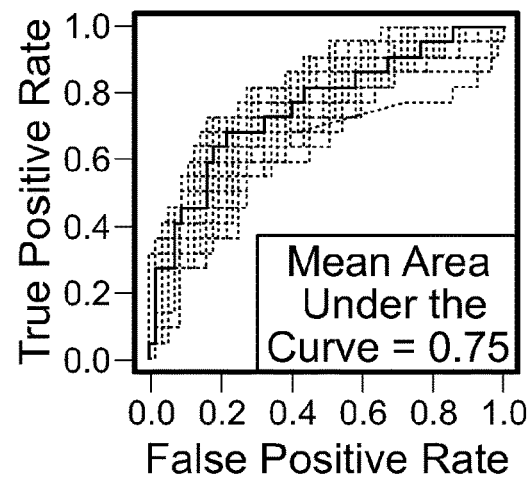

A risk index threshold that best predicted recurrence with LOO cross-validation was determined. Each held-out sample was treated as a new patient on whom we tested and subsequently refined the optimal index cutoff to separate patients with recurrence vs. no recurrence. This procedure demonstrated that the sensitivity of a risk index cutoff of 0.036 to predict recurrence in a new patient was 82% at a specificity of 95%. Furthermore, using another LOO procedure, where the risk index was built 77 times using 76 samples and then tested on the held-out sample, the gut microbiota was a strong predictor of recurrence (permutation test performed on the difference between the mean of those without recurrence and the mean of those with recurrence, of all the held-out samples, with 999 random permutations where the samples are all freely exchangeable; p<0.0001; FIG. 10C).

Figure 11A:
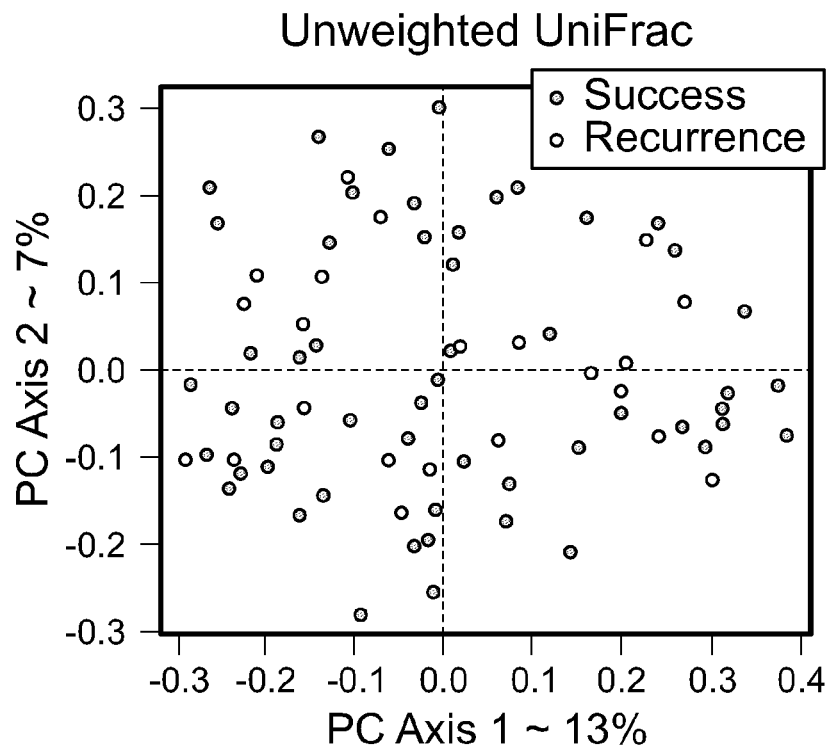
FIGS. 11 A-B show beta-diversity comparisons of the gut microbiomes of the fecal samples collected in responders and non-responders. Analyses performed on 16S rRNA V4 region data, with a rarefaction depth of 6,987 reads per sample. (A) PCoA of unweighted UniFrac distances. Proportion of variance explained by each principal coordinate axis is denoted in the corresponding axis label. (B) PCoA of weighted UniFrac distances. Proportion of variance explained by each principal coordinate axis is denoted in the corresponding axis label. This is no clustering between those with and without recurrence (unweighted UniFrac distance metric: R=-0.0961, p=0.993; weighted UniFrac distance metric: R=0.0165, p=0.331).
Figure 11B:
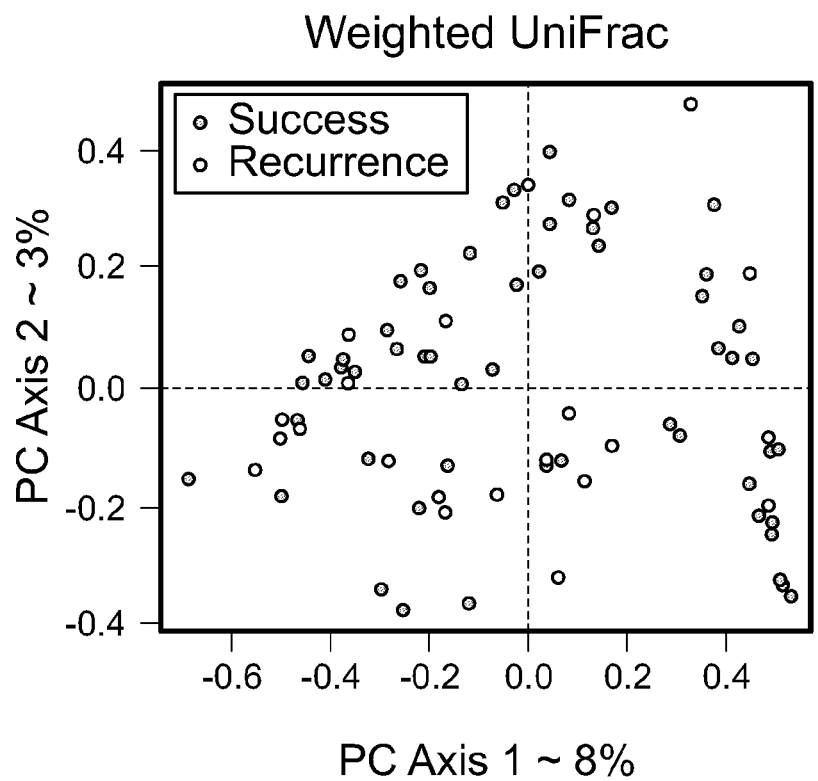
Figure 12:
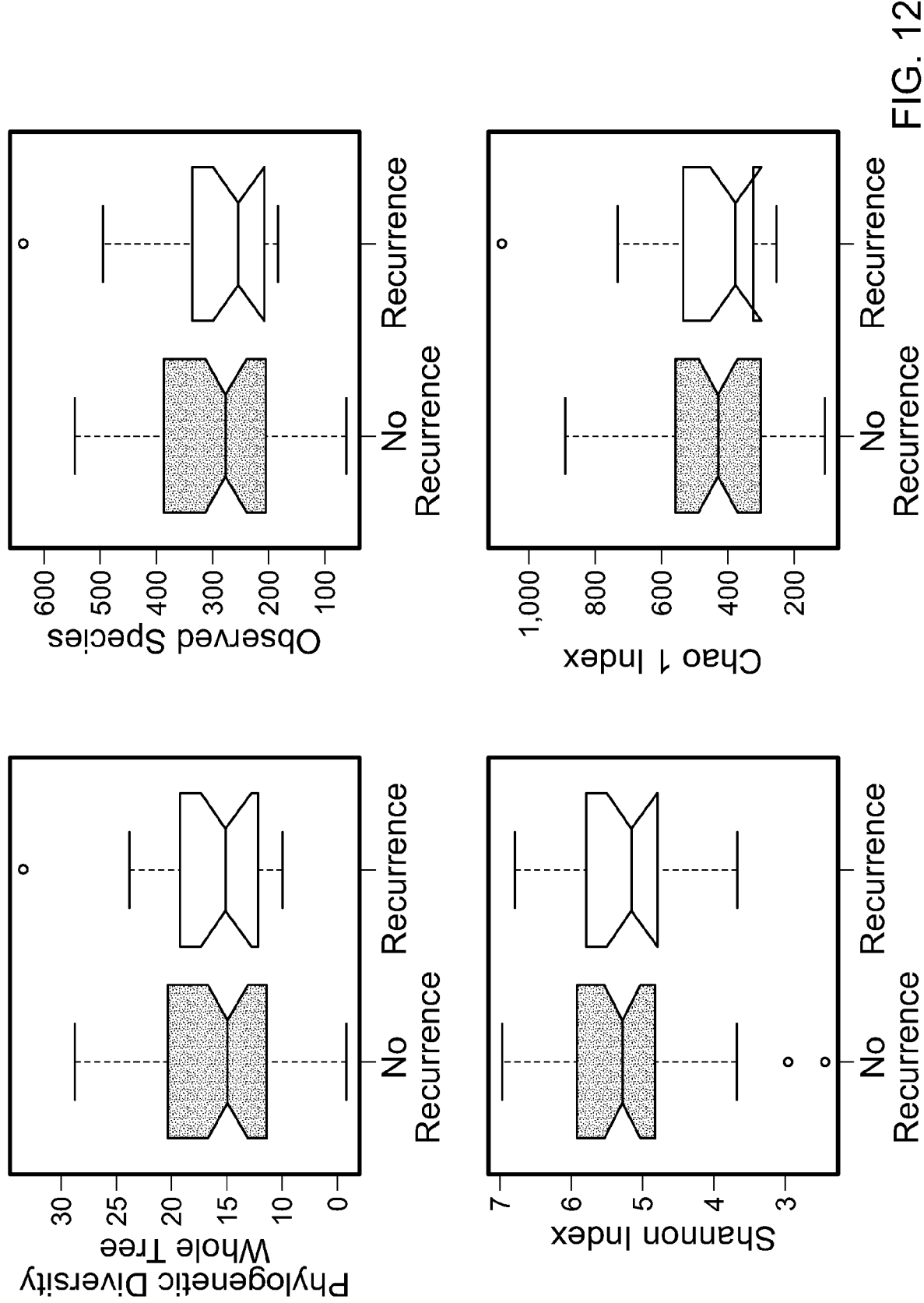
FIG. 12 shows alpha-diversity comparisons of the gut microbiomes of the fecal samples collected in responders and non-responders. Whiskers in the boxplot represent the range of minimum and maximum alpha diversity values within a population, excluding outliers. There was no significant difference in alpha diversity in fecal samples collected from patients with recurrence as compared with alpha diversity from samples collected patients without recurrence, observed with both phylogenetic (Faith's phylogenetic diversity) and nonphylogenetic (observed species, Shannon index, chao 1 index) richness metrics.

Pre-Treatment Gut Microbial Diversity is not Significantly Different in Patients with and without Recurrent CDI Unweighted and weighted UniFrac based PCoA, based on 16S rRNA gene sequencing using MiSeq Illumina platform did not show significant differences between those with and without recurrence (unweighted UniFrac distance metric: R=−0.0961, p=0.993; weighted UniFrac distance metric: R=0.0165, p=0.331) (FIG. 11). Similarly, there was no significant difference in alpha diversity based on four different metrics between those with and without recurrence (FIG. 12).

Figure 13:
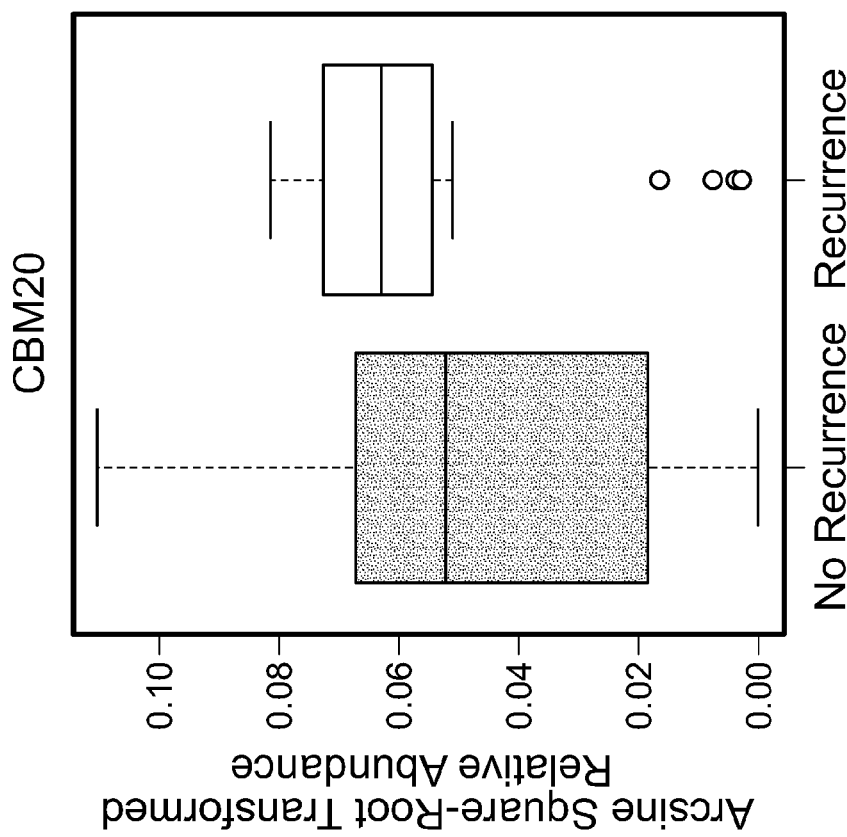
FIG. 13 shows significantly increased carbohydrate-active enzymes GT30 (β-fucosidase) and CBM20 (carbohydrate-binding module) in patients with recurrence compared to patients without recurrence as shown by Mann-Whitney test. Boxplots denote top quartile, median and bottom quartile.
Figure 13:
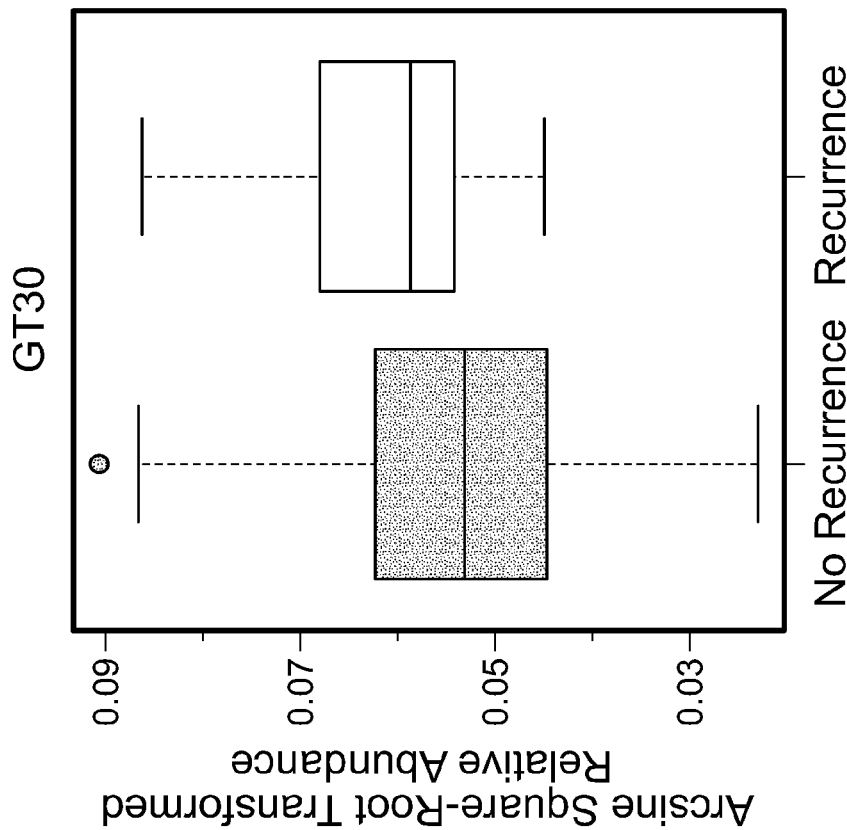

Gut Microbiota Functional Repertoire is Significantly Different in Those with and without Recurrence As described above, PICRUSt was used to predict CAZY GH assignments. Based on the LEfSe tool, it was found that GT30 (β-fucosidase), and a carbohydrate-binding module (CBM20) were increased in patients who had a recurrence compared to patients who did not with LDA score ($\log_{10}$) >2 (FIG. 13).

These results demonstrate that biomarkers, such as the gut microbiota signature and/or the gut microbiota functional repertoire (e.g., polypeptides present in the gut) can predict response to primary CDI treatment, differentiating patients with and without recurrence.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for treating a Clostridium difficile infection (CDI) in a mammal, the method comprising:
    detecting a gut microbiota panel in a fecal sample obtained from the mammal, wherein the gut microbiota panel comprises Veillonella, Enterobacteriaceae, Streptococcus, Parabacteroides, and Lachnospiraceae;
    administering advanced CDI treatment to the mammal if two or more of Veillonella, Enterobacteriaceae, Streptococcus, Parabacteroides, and Lachnospiraceae in the panel are increased relative to a control gut microbiota panel, wherein the advanced CDI treatment is selected from the group consisting of fecal transplantation, immunoglobulin therapy, and defined microbial consortia.

2. The method of claim 1, wherein the *Enterobacteriaceae* is *Enterobacteriaceae erwinia*.

3. The method of claim 1, wherein the *Veillonella* is *Veillonella dispar* or *Veillonella parvula*.

4. The method of claim 1, wherein the *Parabacteroides* is *Parabacteroides distasonis*.

5. The method of claim 1, wherein the detecting comprises isolation of DNA from the fecal sample.

6. The method of claim 5, wherein the detecting comprises identification of operational taxonomic units.

7. The method of claim 5, wherein the detecting comprises 16s sequencing.

8. The method of claim 1, wherein the control gut microbiota panel comprises gut microbiota from one or more mammals that do not have CDI.

9. The method of claim 1, further comprising identifying the mammal as having CDI.

* * * * *